(12) United States Patent
Anisimov et al.

(10) Patent No.: US 7,285,093 B2
(45) Date of Patent: Oct. 23, 2007

(54) SYSTEMS FOR ULTRASONIC IMAGING OF A JAW, METHODS OF USE THEREOF AND COUPLING CUSHIONS SUITED FOR USE IN THE MOUTH

(75) Inventors: Victor Anisimov, St. Petersburg (RU); Dan Cohen, Modiin (IL); Sergei Efimov, Haifa (IL); Alon Eitan, Tel Aviv (IL); Nadav Haas, Merkaz Shapira (IL); Yuval Jacoby, Tel Aviv (IL); Aharon Ocherashvili, Bat Yam (IL); Garri Passi, Ashdod (IL); Boris Pershitz, Moshav Tzufit (IL); Yuval Shay-El, Ramat Gan (IL); Pavel Smirnov, Rishon Letzion (IL); Uri Stein, Rosh Haayin (IL)

(73) Assignee: Imadent Ltd., Rechovot (IL)

( * ) Notice: Subject to any disclaimer, the term of this patent is extended or adjusted under 35 U.S.C. 154(b) by 438 days.

(21) Appl. No.: 10/681,906

(22) Filed: Oct. 10, 2003

(65) Prior Publication Data

US 2004/0143186 A1 Jul. 22, 2004

(51) Int. Cl.
*A61B 8/00* (2006.01)
(52) U.S. Cl. .................................... 600/443
(58) Field of Classification Search ........ 600/437–472; 128/916; 433/2, 24–25, 214, 223, 229
See application file for complete search history.

(56) References Cited

U.S. PATENT DOCUMENTS

| | | | |
|---|---|---|---|
| 4,637,256 A * | 1/1987 | Sugiyama et al. ............ 73/633 |
| 4,913,157 A | 4/1990 | Pratt, Jr. et al. |
| 5,115,813 A * | 5/1992 | Ylander et al. ............. 600/437 |
| 5,278,756 A * | 1/1994 | Lemchen et al. ........... 600/587 |
| 5,368,478 A * | 11/1994 | Andreiko et al. ............. 433/24 |
| 5,427,105 A | 6/1995 | Knapp et al. |
| 5,564,423 A | 10/1996 | Mele et al. |
| 5,651,363 A | 7/1997 | Kaufman et al. |
| 6,030,221 A | 2/2000 | Jones et al. |
| 6,050,821 A * | 4/2000 | Klaassen et al. ............ 433/214 |
| 6,081,739 A * | 6/2000 | Lemchen .................... 600/407 |
| 6,086,538 A | 7/2000 | Jorgensen et al. |
| 6,402,707 B1 | 6/2002 | Ernst |
| 6,589,054 B2 * | 7/2003 | Tingley et al. .............. 433/215 |
| 6,638,219 B1 * | 10/2003 | Asch et al. ................. 600/437 |

FOREIGN PATENT DOCUMENTS

| | | |
|---|---|---|
| DE | 4205360 | 2/1992 |
| DE | 19921279 | 5/1999 |
| WO | WO 02/085178 | 10/2002 |

* cited by examiner

*Primary Examiner*—Francis J. Jaworski

(57) ABSTRACT

Systems and methods for ultrasonic imaging of a jaw and coupling cushions suited for use in the mouth. The system includes a specially configured ultrasonic probe, a position locator module for defining a probe location and transmitting the definition to a central processing unit (CPU) and the CPU. The CPU is capable of receiving digital data from transducers in the probe and receiving the location of the probe and producing an image of at least a portion of a jaw. The method includes providing the ultrasonic probe, defining its location and communicating the location to a CPU and transmitting an signal from a transducer and receiving at least a portion of the signal at at least one of the transducers. The CPU receives transducer data and a location of the probe and produces an image of the at least a portion of the jaw. An ultrasonic coupling cushion is further disclosed.

11 Claims, 26 Drawing Sheets

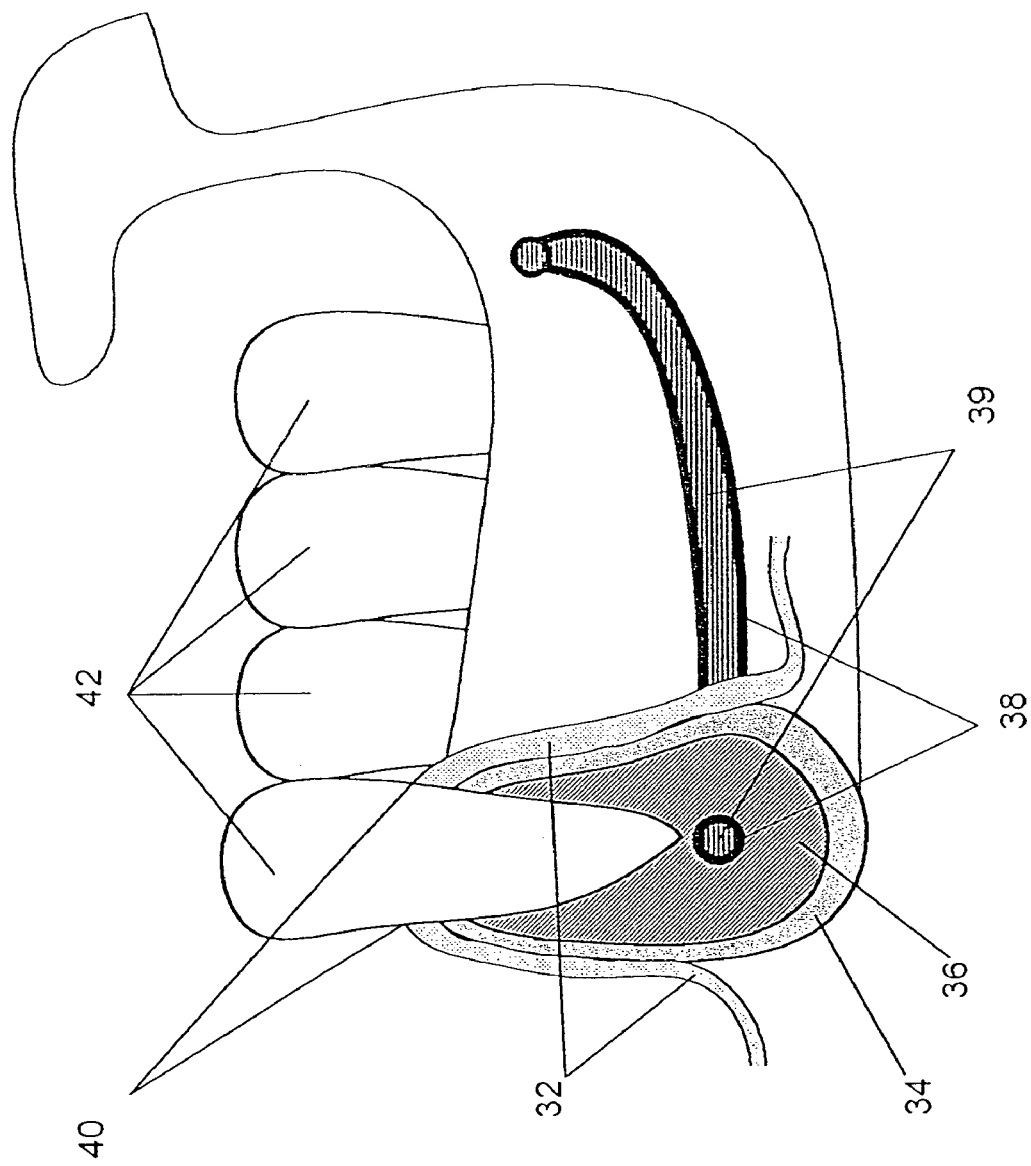

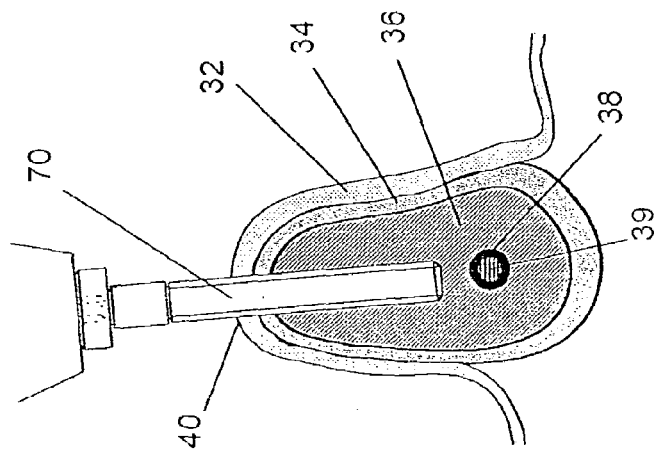
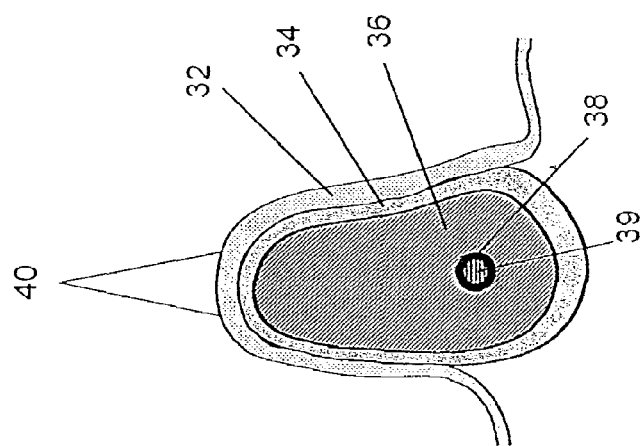
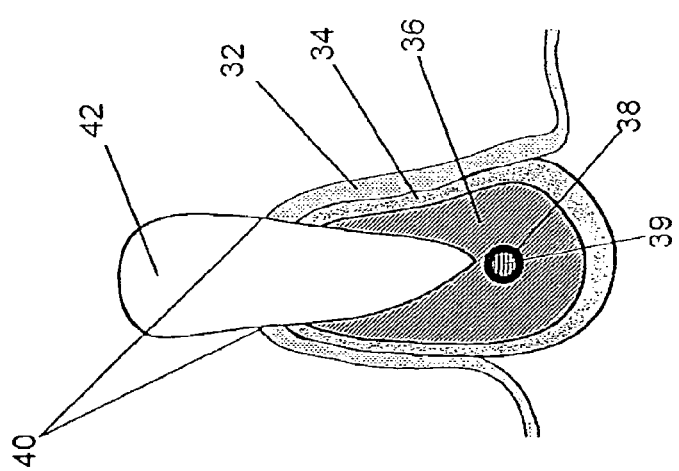

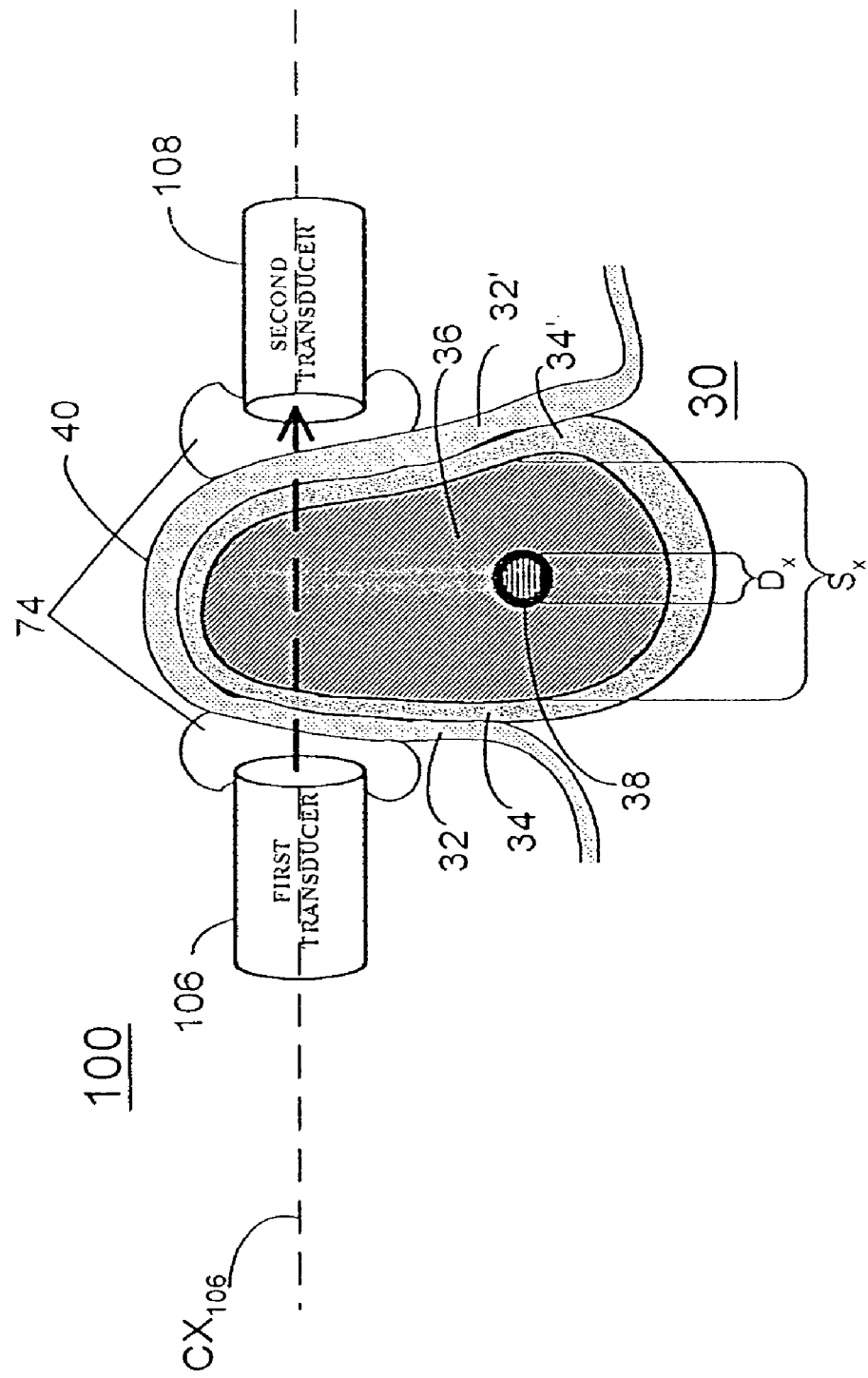

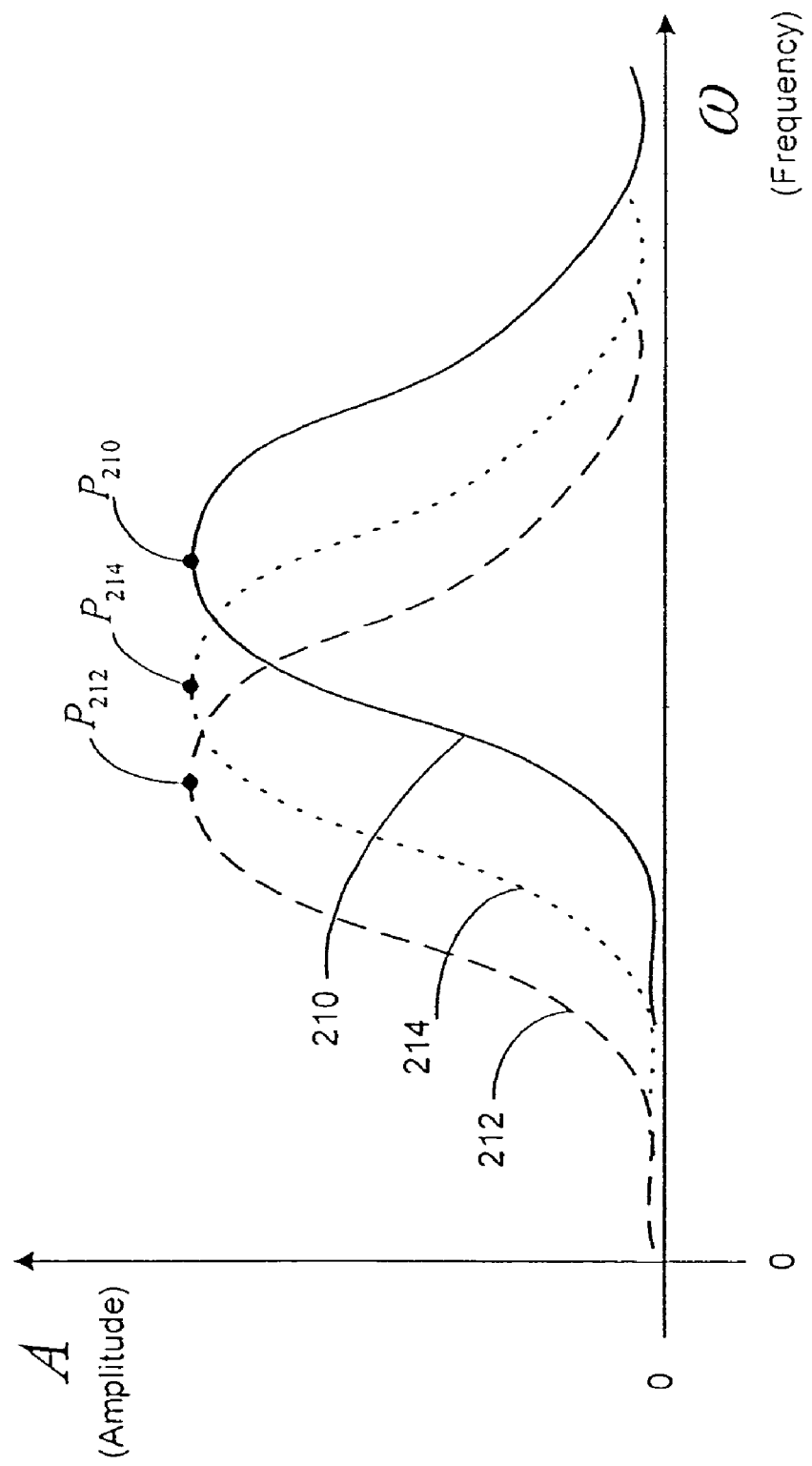

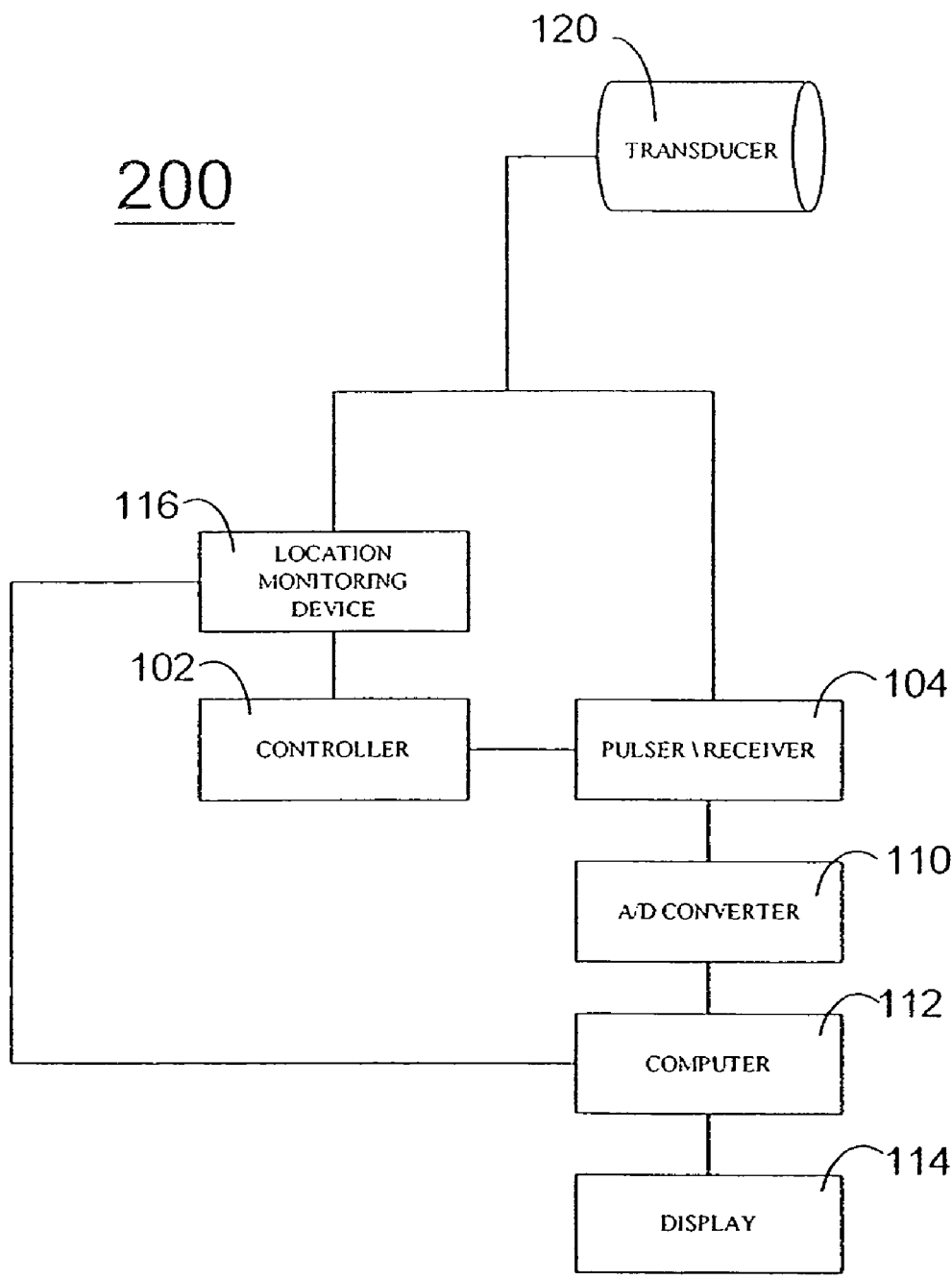

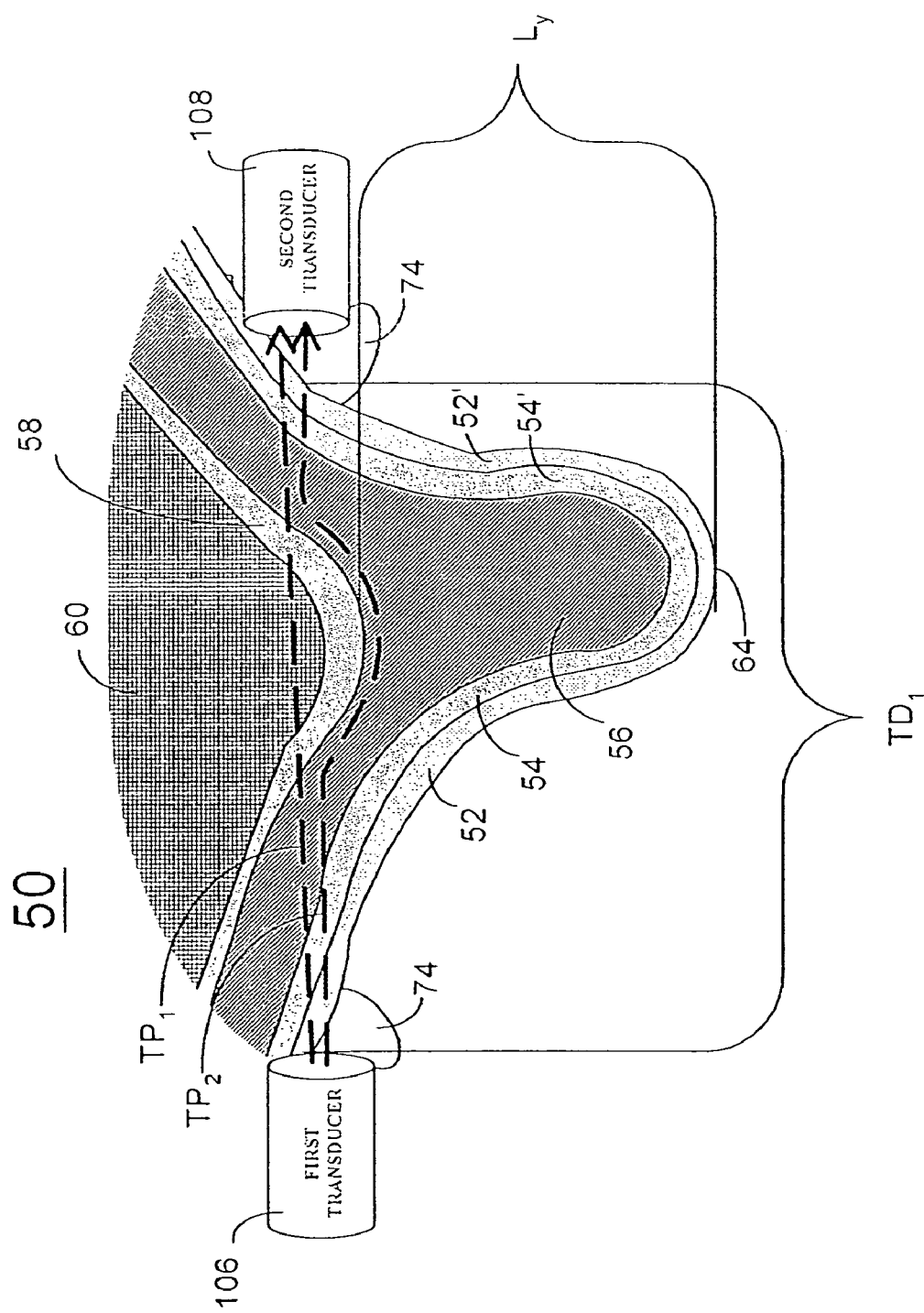

FIGURE 22a U22
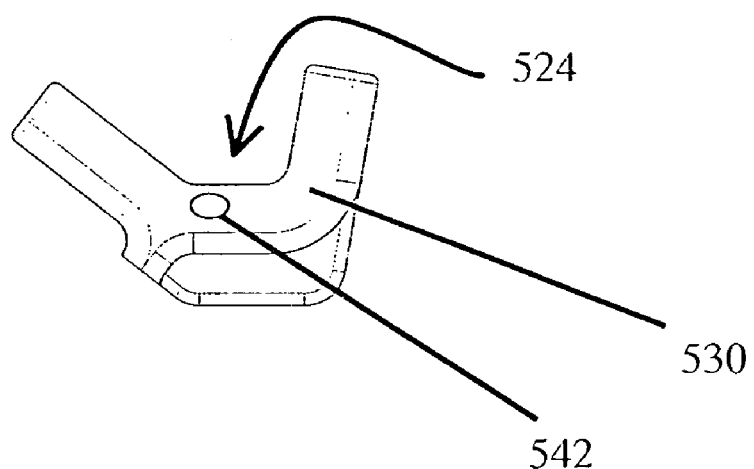
FIGURE 22b 522
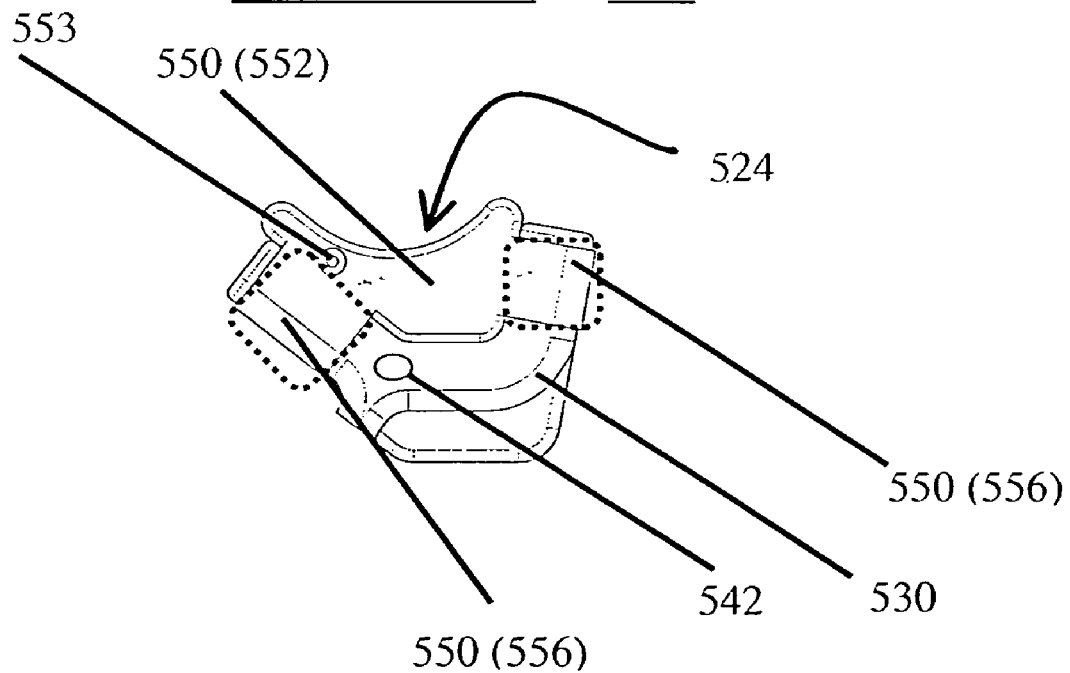

SYSTEMS FOR ULTRASONIC IMAGING OF A JAW, METHODS OF USE THEREOF AND COUPLING CUSHIONS SUITED FOR USE IN THE MOUTH

CROSS-REFERENCE TO RELATED APPLICATIONS

This application claims priority from PCT application IL02/00311 filed on Apr. 18, 2002 and from U.S. Provisional Application No. 60/284,918 filed Apr. 20, 2001.

FIELD AND BACKGROUND OF INVENTION

The present invention relates systems for ultrasonic imaging of a jaw, methods of use thereof and coupling cushions suited for use in the mouth. Specifically the invention relates to systems which employ improved proe configurations which permit imaging of the mandible and maxilla and facilitate visualization of bone and nerve canals.

Diagnostic imaging of hard tissue has numerous practical uses in various medical fields. In the fields of Dentistry, Dental Surgery and Implantology, for example, X-ray and CT imaging are extensively used for imaging the human upper and lower jaws. However, such imaging techniques suffer from several significant disadvantages. In order to illustrate the deficiencies of current day techniques for imaging hard tissue, let us consider, for example, existing jaw imaging techniques used today in dental implant surgery.

In many mammals, including humans, the jaws (upper and lower) comprise several layers of tissue. FIG. 1 shows a high-level schematic sectional view of a human lower jaw, or mandible 30. The external layer of mandible 30 comprises the gum 32, or the mucoperiosteal tissue covering the jawbone. Beneath gum 32 is a layer of cortical (compact) bone 34, which is normally dense bone tissue. Beneath cortical bone 34 lies an area of trabecular bone 36, which is normally bone tissue softer than cortical bone. Within the area of trabecular bone and along the mandibular jaw, runs the mandibular canal 38 carrying the inferior alveolar nerve 39. Mandibular canal 38 is an elongated tubular cavity of varying density, usually comprising dense (cortical type bone) borders. In cases where dense borders are not present, mandibular canal 38 is a conduit within a sponge-like matrix. In the latter case, mandibular canal cavity 38 may be distinguished from the cavities of the trabecular environment 36 by the mandibular canal's regular shape, i.e. an elongated tubular cavity. All cavities inside the cross-section of mandible 30 are normally filled with fluids. The upper region of the mandible forms the alveolar ridge 40 in which teeth 42 are normally situated.

FIG. 2a shows a low-level schematic sectional view of mandible 30. As mentioned hereinabove, in a normal situation alveolar ridge 40 comprises sockets housing teeth 42. FIG. 2b shows a sectional view of mandible 30 after the loss of a tooth, for example, due to tooth extraction. It is well known that following the loss of a tooth, the residual socket in alveolar ridge 40 regenerates and fills with hard tissue. The procedure of replacing a tooth with an implant-supported prosthesis has become very common and widely used. The process of fixture (implant) placement entails exposing the bone (raising the mucoperiosteal flap), and drilling a receptive site for the fixture. FIG. 2c shows a sectional view of mandible 30 with a drill 70 drilling into the alveolar ridge 40. The common procedure prior to installation of a dental fixture involves, inter alia, drilling into the cortical 34 and trabecular 36 bone of mandible 30 using a drill 70, in order to prepare a socket in which a fixture will be anchored. If an implantologist drilling into mandible 30 is not aware of the topology and internal structure thereof (e.g. precise location of mandibular canal 38) then during the drilling procedure drill 70 may contact and damage mandibular canal 38 and inferior alveolar nerve 39 situated therein, or drill outside the bone boundaries. Such damage can ultimately lead to severe pain, hemorrhage and even local paralysis, among other undesired consequences. For this reason, it is widely acknowledged that an implantologist must obtain an internal image of the mandible prior to performing the implant surgery.

Similarly, when planning implant surgery on a human upper jaw, or maxilla, an implantologist will also need to obtain an internal image of the jaw. FIG. 3a shows a schematic sectional view of a maxilla 50. The maxilla comprises an external layer of gum 52, under which lies a layer of cortical bone 54, enclosing an area of trabecular bone 56. Under trabecular bone 56 lies another layer of cortical bone 58 which serves as the floor of the signal and\or nasal cavities 60. In a normal (healthy) maxilla, a tooth 62 is anchored in the cortical 54 and trabecular-56 bone. FIG. 3b shows a sectional view of maxilla 50 after the loss of tooth 62, for example, due to tooth extraction. When preparing a receptive site for a fixture in maxilla 50, the implantologist uses a drill 72 in order to drill a hole through the cortical 54 and trabecular 56 bone. However, if the implantologist is not aware of the internal structure and shape of the jawbone (e.g. the location of signal and/or nasal cavities 60), the implantologist may perforate and damage cortical floor 58. Such perforation may lead to a serious signal infection and hemorrhage, as well as other undesired consequences. It is therefore common practice to obtain an internal image of the maxilla prior to the implant surgery.

The most common technique currently used in Implantology for imaging the lower and\or upper jaw is Panoramic X-ray Radiography. FIG. 4 is an example of a panoramic x-ray image of human upper and lower jaws. In the lower jaw, mandibular canal 38 (black) appears inside trabecular bone area 36 (gray). A cortical bone layer 34 (white) encloses trabecular bone area 36. In the upper jaw, signal and nasal cavities 60 (black) appear above cortical floor 58 (white), which is above trabecular bone area 56 (gray), under which lies cortical bone layer 54 (white).

The panoramic X-ray technique suffers from some significant shortcomings. First, it is well established that X-ray radiation is hazardous to the health of the patient. Second, panoramic X-ray produces a two-dimensional image of the jaw, which is perpendicular to a cross-section of the jaw. This limitation makes the panoramic image unreliable for guiding the implantologist to drill within the bone boundaries and within a safe distance from the mandibular canal, or the signal\nasal cavities. The panoramic image is inherently distorted and inaccurate because it projects the three-dimensional jaw into a two-dimensional image. This image is therefore unreliable also for assessing the depth of the bone tissue available for drilling and preparing a fixture. Third, the image is not taken chair-side and consequently, panoramic X-ray does not allow for real-time monitoring of implant procedures. All of the above disadvantages make the panoramic X-ray image a hazardous, imprecise, and unreliable imaging solution.

Another imaging technique used in Implantology, though less common, is Computerized Tomography (CT). FIG. 5a is an example of a sectional CT image of a toothless mandible 30. Cortical layer 34 (white) encloses trabecular area 36 (gray), which surrounds mandibular canal 38 (black ellipse). FIG. 5*b* is an example of a toothless maxilla 50. Cortical layer 54 (white) covers trabecular area 56 (gray). Cortical floor 58 (white) borders signal and nasal cavities 60 (black).

A CT image of an upper or lower jaw provides a sectional view of the jaw, and is less distorted than panoramic radiography. However, CT involves a substantially higher dosage of X-ray radiation than conventional radiography, and therefore poses a significantly greater risk to the health of the patient. Furthermore, CT equipment is very expensive and is only rarely found inside the clinic of the implantologist. CT can definitely not provide a chair-side imaging solution.

The popularity of ultrasonic medical diagnostic systems has significantly risen in recent years. In contrast to X-ray and CT systems, ultrasonic systems have the advantage of not exposing the patient or doctor to hazardous ionizing radiation, and are generally more compact and economical. In the field of Dentistry and Dental Implantology various ultrasonic diagnostic and measurement systems are known.

International patent application PCT/IL00/00341 publication no. WO 01/00102 entitled "Alveolar Bone Measurement System" (hereunder "ABMS"), which is fully incorporated herein by reference, discloses an ultrasound system for assessment of distance between an area of interest and a known location of a non-bone canal for use in drilling an implant receiving cavity in the alveolar bone of a human subject's posterior mandible or posterior maxilla. ABMS comprises an ultrasound probe capable of being introduced at the area of interest and transceiving pulse echo ultrasound signal to the alveolar bone and therefrom and an electronic circuitry for processing the ultrasound signal and providing an indication of the remaining alveolar bone distance between the ultrasound probe and a canal within the alveolar bone.

However, ABMS still comes short of answering the needs of the dental implantologist for the following reasons. First, measurement of time-of-flight (TOF) from a location on the surface of the alveolar bone to a non-bone canal inside the jaw is, in reality, impracticable or at least very imprecise due to the high level of attenuation and scattering inside the jawbone. Although the application further discloses an improved method in which a second TOF measurement is taken after drilling a bore of known depth, the improvement is still subject to the aforementioned attenuation and scattering problem, and moreover, as mentioned in the ABMS patent application itself (page 2 line 1) it is of significance that the condition of the jaw be assessed prior to drilling. Second, ABMS relies on the so-called "average velocity of ultrasound within bone tissue, as known, per se" (page 4, line 14). However, it is known that the velocity of ultrasound may vary from patient to patient, and from bone to bone within a certain patient, and even in different regions of a certain bone. Thus, even in the case that ABMS manages to take a precise TOF measurement, it will still not be able to calculate the precise distance from the probe to the canal due to an error in the velocity of ultrasound. Third, ABMS does not disclose any mechanism or procedure for ensuring that the echo which is supposedly from the canal and on which the distance measurement is based, is really from the canal and not from another reflector inside the jawbone. Fourth, ABMS is limited to measuring the distance from the canal to the alveolar bone, and does not teach how to measure the distance between the canal and the buccal and lingual walls of the jawbone, which is of significant importance to the implantologist, e.g. in order to determine an optimal angle of drilling. Lastly, being a measurement system rather than an imaging system, the most ABMS can provide is a numerical distance measurement from the location where the probe is located to a canal within the bone, but no implantologist will suffice with a mere numerical value as a basis for planning or performing a drill into a jaw.

German Patent No. DE 19921279 (hereunder "the '279 patent"), which is fully incorporated herein by reference, discloses a surgical instrument for drilling into a bone, the instrument comprising an ultrasonic transducer for transmitting and receiving ultrasonic waves. The transducer is connected to a device which generates signals according to the intensity and TOF of ultrasonic energy received by the transducer, and these signals provide measurements for determining the characteristics of the bone in the direction of transmission. The '279 patent suffers from limitations similar to those of ABMS, namely, impracticable or imprecise measurement and insufficient information to the implantologist.

U.S. Pat. No. 6,030,221 entitled "Ultrasonic Apparatus and for Precisely Locating Cavitations within Jawbones and the Like" (hereunder "the '221 patent"), which is fully incorporated herein by reference, discloses an apparatus which generates an ultrasonic pulse and passes the pulse through the jawbone of a human. The pulse is detected by an ultrasonic receiving unit. Attenuations in the amplitude of the pulse are detected and displayed on a color monitor. The color monitor allows the detection of cavitations by interpreting color codes in a 4×4 matrix displayed oil the monitor.

U.S. Pat. No. 6,086,538 entitled "Methods and Apparatus for Evaluation of Bone Condition" (hereunder "the '538 patent") discloses a method of evaluating the status of bone tissue, useful in the diagnosis of osteoporosis, in which a calcaneus is scanned in through-transmission mode, and a characteristic of ultrasound, such as the speed-of-sound or attenuation, is measured in different locations. The location of a circular (as seen from the side) area of reduced attenuation inside the calcaneus is derived from the ultrasound measurements, and finally the status of the examined bone tissue is evaluated based on the measurements which were taken in that circular area.

Both the '221 patent and the '538 patent concentrate on the problem of assessing the quality or health of the bone under examination rather than providing an image of the bone for guidance in a medical procedure. As a result, both these patents provide only a two-dimensional attenuation map of the examined bone which is perpendicular to a cross-section of the bone, and furthermore, include no mechanism or procedure for precisely calculating the distance of the detected cavitations (in the case of the '221 patent) or the circular area of reduced attenuation (in the case of the '538 patent) in relation to a reference point of interest. As mentioned hereinabove in connection to the panoramic X-ray technique, a lateral two-dimensional image is unreliable for guiding the implantologist to drill within the bone boundaries and within a safe distance from the mandibular canal, or the signal/nasal cavities.

German Patent No. DE 4205360 (hereunder "the '360 patent"), which is fully incorporated herein by reference, discloses an ultrasonic measuring gauge for determining jawbone width. U.S. Pat. No. 5,427,105 entitled "Measuring Procedure for the Thickness of the Mucous Membrane of an Alveolar Process" (hereunder "the '105 patent"), which is fully incorporated herein by reference, discloses an ultrasonic method for measuring the thickness of the mucous membrane in the region of the jawbone ridge. Neither the '360 patent nor the '105 patent comprise any mechanism for scanning the bone being examined. Neither patent provides an image of the bone, nor any information regarding the internal structure of the examined jawbone.

U.S. Pat. No. 5,564,423 entitled "Ultrasonic Measurement System for the Determination of Bone Density and Structure" (hereunder "the '423 patent"), which is fully incorporated herein by reference, discloses an electronic system for measuring the density and structure of bone, equipped with ultrasonic calipers designed to be applied to a segment of the human body (for example, a finger) containing bone tissue to be examined. The ultrasonic calipers include a transmitting transducer and a receiving transducer, which enable measuring TOF in the bone tissue based on a through-transmission method. The system provides an indication of the density and structure of the bone tissue based on the measured TOF. Since the '423 patent relies on TOF measurement, it suffers from the same impracticability and inaccuracy problems mentioned above in connection to ABMS. Likewise, the '423 patent also does not comprise any mechanism for scanning the examined bone tissue, and does not provide the location and image of internal structures within the bone tissue.

Thus, none of the above solutions provides an economic, radiation free, real-time, chair-side imaging tool to the implantologist. Ongoing monitoring of the drilling process allows for depth and angulation corrections on the fly. There is thus a widely recognized need for, and it would be highly advantageous to have systems for ultrasonic imaging of a jaw, methods of use thereof and coupling cushions suited for use in the mouth devoid of the above limitations.

SUMMARY OF THE INVENTION

According to one aspect of the present invention there is provided an improved ultrasonic imaging system constructed to facilitate imaging of at least a portion of a jaw. The system includes: (a) a probe, the probe includes at least one array of ultrasonic transducers; (b) a position locator module designed and constructed to be capable of defining a location of the probe in six degrees of freedom and transmitting the definition to a central processing unit; and (c) the central processing unit. The Central processing unit (CPU) is capable of, by virtue of design and configuration, (i) receiving from the probe digital data from each of the ultrasonic transducers in the arrays; (ii) further receiving from the position locator a location of the probe; and (iii) transforming the digital data into an image of the at least a portion of a jaw.

According to another aspect of the present invention there is provided a method of producing an ultrasonic image of at least a portion of a jaw. The method includes: (a) providing a probe, the probe includes at least one array of ultrasonic transducers; (b) defining a location of the probe in six degrees of freedom by means of a position locator; (c) communicating the location to a central processing unit; (d) transmitting an ultrasonic signal from at least one of the transducers and receiving at least a portion of the ultrasonic signal at least one of the transducers; and (e) employing a central processing unit. The central processing unit serves to; (i) receive a set of digital data pertaining to the transmitting and receiving performed by the transducers of in the arrays of the probe; (ii) further receive from the position locator a location of the probe; and (iii) transform the digital data into an image of the at least a portion of the jaw.

According to yet another aspect of the present invention there is provided an ultrasonic coupling cushion, the cushion includes an elastic container capable of retaining a coupling medium wherein the elastic container is designed and constructed to be insertable in a mouth of a subject.

According to further features in preferred embodiments of the invention described below, the image is a three dimensional image. The image preferably depicts mandibular Features such as bones, teeth and nerve canals.

According to still further features in the described preferred embodiments the probe is a mandibular probe designed and constructed to facilitate imaging of at least a portion of a lower jaw. The mandibular probe includes: (i) a first array of ultrasonic transducers mounted upon a first wand, the first array of ultrasonic transducers positionable distal to the lower jaw and outside of a mouth; (ii) a second array of ultrasonic transducers, the second array of transducers mounted upon a second wand, the second array of ultrasonic transducers positionable proximal to the lower jaw and inside of the mouth; and (iii) at least one connective member. The connective member designed and constructed to connect the first and second wands one to another and to allow relative positioning thereof. The connective member includes an assembly designed and constructed to attach the first and second wands and facilitate translational motion of the wands with respect to one another.

According to still further features in the described preferred embodiments the probe is designed and constructed to facilitate imaging of at least a portion of an upper jaw and includes a single curved array of ultrasonic transducers mounted upon a wand, the wand designed and constructed to be insertable into a mouth of a patient.

According to still further features in the described preferred embodiments the position locator module includes at least one first position sensor located on the probe and at least one second position sensor located on a head of a subject.

According to still further features in the described preferred embodiments the position locator module includes a first mechanical positioning mechanism designed and constructed to position the probe and a retention means designed and constructed to engage and retain a head (of a subject in a known position.

According to still further features in the described preferred embodiments the system further includes an ultrasonic coupling cushion, the cushion includes an elastic container capable of retaining a coupling medium. The elastic container is designed and constructed to be insertable in a mouth of a subject.

According to still further features in the described preferred embodiments the image is a three dimensional image.

According to still further features in the described preferred embodiments providing a probe includes providing a mandibular probe designed and constructed to facilitate imaging of at least a portion of a lower jaw and includes: (i) providing a first array of ultrasonic transducers mounted upon a first wand, the first array of ultrasonic transducers positionable distal to the lower jaw and outside of a mouth; (ii) providing a second array of ultrasonic transducers, the second array of transducers mounted upon a second wand, the second array of ultrasonic transducers positionable proximal to the lower jaw and inside of the mouth; (iii) providing at least one connective member, the connective member designed and constructed to connect the first and second arrays one to another and to allow relative positioning thereof. The connective member includes an assembly designed and constructed to attach the first and second wands and facilitate translational motion of the wands with respect to one another.

According to still further features in the described preferred embodiments providing a probe includes providing a maxillary probe designed and constructed to facilitate imaging of at least a portion of an upper jaw and includes and includes a single curved array of ultrasonic transducers mounted upon a wand, said wand designed and constructed to be insertable into a mouth of a patient.

According to still further features in the described preferred embodiments the coupling cushion further includes the coupling medium. The coupling medium is selected from the group consisting of water, an aqueous solution, a gel and a polymer solution.

According to still further features in the described preferred embodiments the elastic container further includes attachment device designed and constructed to engage and retain at least a portion of an ultrasonic probe. The attachment device may be, for example a sleeve, a pocket or series of loops. The attachment device includes at least one hole to accept an ultrasonic probe.

The present invention discloses a method and apparatus for non-invasive ultrasonic imaging of hard tissue.

According to the present invention, there is provided in a first embodiment, a method of ultrasonic imaging of a biological tissue, comprising the steps of scanning the biological tissue with ultrasonic energy transmitted from and received at a plurality of known transmittal and reception locations about the biological tissue, to obtain a corresponding plurality of sets of digital data, and processing the sets of digital data to produce an image of a cross-section of the biological tissue.

According to yet another feature of the first embodiment of the method of the present invention, the step of scanning includes applying at least one scanning mode selected from the group consisting of through-transmission mode and pulse-echo mode.

According to yet another feature of the first embodiment of the method of the present invention, the step of scanning includes using at least one scanning mechanism selected from the group consisting of mechanical scanning and electronic scanning.

According to yet another feature of the first embodiment of the method of the present invention, the step of scanning includes the substeps of disposing at least one ultrasonic transducer in proximity to the biological tissue, determining a location of the at least one ultrasonic transducer, transmitting ultrasonic energy into the biological tissue using the at least one ultrasonic transducer, the ultrasonic energy being reflected from the biological tissue, and receiving the ultrasonic energy reflected from the biological tissue using the at least one ultrasonic transducer.

According to additional features in the first embodiment of the method of the present invention, the method further includes changing the location of the at least one ultrasonic transducer, and repeating the steps of: determining a location of the at least one ultrasonic transducer, transmitting ultrasonic energy into the biological tissue using the at least one ultrasonic transducer, the ultrasonic energy being reflected from the biological tissue, and receiving the ultrasonic energy reflected from the biological tissue using the at least one ultrasonic transducer for a desired number of repetitions.

According to a second embodiment of the method of the present invention, the step of scanning includes the substeps of disposing a plurality of ultrasonic transducers in proximity to the biological tissue, determining a location of each of the plurality of ultrasonic transducers, transmitting ultrasonic energy into the biological tissue, using at least one first ultrasonic transducer selected from the plurality of ultrasonic transducers, the ultrasonic energy propagating through the biological tissue, and receiving the through propagating ultrasonic energy, using at least one second ultrasonic transducer selected from the plurality of ultrasonic transducers, the at least one second ultrasonic transducer being different from the at least one first ultrasonic transducer.

According to additional features in the second embodiment of the method of the present invention, the method further includes the substeps of varying the selection of at least one ultrasonic transducer from the group consisting of the at least one first ultrasonic transducer and the at least one second ultrasonic transducer, and repeating the steps of: determining a location of each of the plurality of ultrasonic transducers, transmitting ultrasonic energy into the biological tissue, using at least one first ultrasonic transducer selected from the plurality of ultrasonic transducers, the ultrasonic energy propagating through the biological tissue, and receiving the through propagating ultrasonic energy, using at least one second ultrasonic transducer selected from the plurality of ultrasonic transducers, the at least one second ultrasonic transducer being different from the at least one first ultrasonic transducer, for a desired number of repetitions.

According to a third embodiment of the method of the present invention, the step of scanning includes the substeps of: (a) disposing a plurality of ultrasonic transducers in proximity to the biological tissue, (b) determining a location of each of the plurality of ultrasonic transducers, (c) transmitting ultrasonic energy into the biological tissue, using at least one ultrasonic transducer selected from the plurality of ultrasonic transducers, the ultrasonic energy being reflected from the biological tissue, (d) receiving the ultrasonic energy reflected from the biological tissue using the same at least one selected ultrasonic transducer used for transmitting, (e) varying the selection of the at least one selected ultrasonic transducer used for transmitting and receiving the ultrasonic energy; and repeating steps (c) through (e) for a desired number of repetitions.

According to the present invention, the substep of generating a spectral function further includes the substep of representing each spectral function by a first representative value, all such first representative values forming a first array of representative values.

According to another feature in the method of the present invention, the first representative value is selected from the group consisting of a minimum, a maximum, an average, a root mean square (RMS), and a total sum of amplitudes.

According to yet another feature in the method of the present invention, the substep of representing each spectral function by a first representative value further includes the substeps of identifying at least one distinct local variability in the first array of representative values, and calculating the value of a dimension related to an internal structure within the biological tissue, based on the at least one distinct local variability.

According to yet another feature in the method of the present invention, the dimension related to an internal structure within the biological tissue is selected from the group consisting of a width, a length, a depth, a height, a diameter and a thickness.

According to yet another feature in the method of the present invention, the internal structure includes a cavity.

According to yet another feature in the method of the present invention, the step of generating a spectral function further includes the substeps of representing each spectral function by a second representative value, all such second representative values forming a second array of representative value, and producing a synthetic array of representative values, based on the first and second arrays of representative values.

According to yet another feature in the method of the present invention, the step of generating a spectral function further includes the substeps of identifying at least one distinct local variability in the synthetic array of representative values, and calculating the value of a dimension related to an internal structure within the biological tissue, based on the at least one distinct local variability.

According to yet another feature in the method of the present invention, the substep of representing each spectral function by a first representative value further includes the substeps of identifying at least one extreme value in the first array of representative values, measuring a first attenuation coefficient inside the biological tissue, measuring a second attenuation coefficient inside an internal structure within the biological tissue, measuring the value of a first dimension related to the biological tissue, and calculating the value of a second dimension related to the internal structure, based on the at least one identified extreme value, the first attenuation coefficient, the second attenuation coefficient, and the value of the first dimension.

According to the present invention, in a fourth embodiment of the method, the step of processing includes the substeps of deriving, from each of the sets of digital data, a property value related to an ultrasonic property of the biological tissue, measuring, for each of the sets of digital data, a dimension value of a dimension related to the biological tissue and to same set of digital data, and calculating, for each of the sets of digital data, a set ratio between the property value and the dimension value.

According to the present invention, in the fourth embodiment of the method, the step of processing further includes the substeps of forming an array of ratios based on the set ratios calculated for all the sets of digital data, identifying at least one distinct local variability in the array of ratios, and calculating the value of a dimension related to an internal structure within the biological tissue, based on the at least one identified distinct local variability.

According to the present invention, in the various embodiments of the method, the step of processing includes deriving, from each of the sets of digital data, at least one value related to an ultrasonic property of the biological tissue.

According to the present invention, in the various embodiments of the method the ultrasonic property includes ultrasonic attenuation.

According to the present invention, in the various embodiments of the method, the step of processing includes the substep of generating, for each of the sets of digital data, a spectral function of the corresponding to the received ultrasonic energy.

According to the present invention, in the various embodiments of the method, the substep of generating a spectral function includes applying a fast Fourier transform (FFT) algorithm.

According to the present invention, in the various embodiments of the method, the step of processing includes applying a Radon transform algorithm.

According to one feature of all embodiments of the method of the present invention, the biological tissue includes a jaw.

According to another feature of all embodiments of the method of the present invention, the biological tissue includes a bone.

According to yet another feature of all embodiments of the method of the present invention, the bone is selected from the group consisting of a mandible and a maxilla.

According to the present invention, there is provided an apparatus for ultrasonic imaging of a biological tissue, comprising means for scanning the biological tissue with ultrasonic energy from a plurality of transmittal and reception locations about the biological tissue, means for determining the transmittal and reception locations, means for generating a plurality of sets of digital data, the sets of digital data representing parameters of the ultrasonic energy at each of the plurality of transmittal and reception locations, and means for processing the plurality of sets of digital data to produce a cross-sectional image of the biological tissue.

The present invention successfully addresses the shortcomings of the presently known configurations by providing systems including specially configured oral ultrasonic probes suitable for use in the mouth as well as coupling cushions for use with these probes and methods for their use.

Implementation of the method and system for ultrasonic imaging of the jaw of the present invention involves performing or completing selected tasks or steps manually, automatically, or a combination thereof. Moreover, according to actual instrumentation and equipment of preferred embodiments of the method and system of the present invention, several selected steps could be implemented by hardware or by software on any operating system of any firmware or a combination thereof. For example, as hardware, selected steps of the invention could be implemented as a chip or a circuit. As software, selected steps of the invention could be implemented as a plurality of software instructions being executed by a computer using any suitable operating system. In any case, selected steps of the method and system of the invention could be described as being performed by a data processor, such as a computing platform for executing a plurality of instructions.

BRIEF DESCRIPTION OF THE DRAWINGS

The invention is herein described, by way of example only, with reference to the accompanying drawings. With specific reference now to the drawings in detail, it is stressed that the particulars shown are by way of example, and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIG. 1 shows a high-level schematic sectional view of a mandible;

FIG. 2a shows a low-level schematic sectional view of a mandible;

FIG. 2b shows a sectional view of a mandible after the loss of a tooth;

FIG. 2c shouts a sectional view of a mandible with a drill drilling into the alveolar ridge;

FIG. 7 illustrates the preferred method of operation of the preferred embodiment apparatus of the present invention;

FIG. 10 illustrates an example of three spectral functions of an ultrasonic signal transmitted through a jaw;

FIG. 11 illustrates an alternative embodiment apparatus of the present invention;

FIG. 15 illustrates an example of two travel paths of ultrasonic pulses propagating through a maxilla;

FIGS. 22a and 22b illustrate a maxillary probe according to the present invention;

DETAILED DESCRIPTION OF THE PREFERRED EMBODIMENTS

Figure 3A:
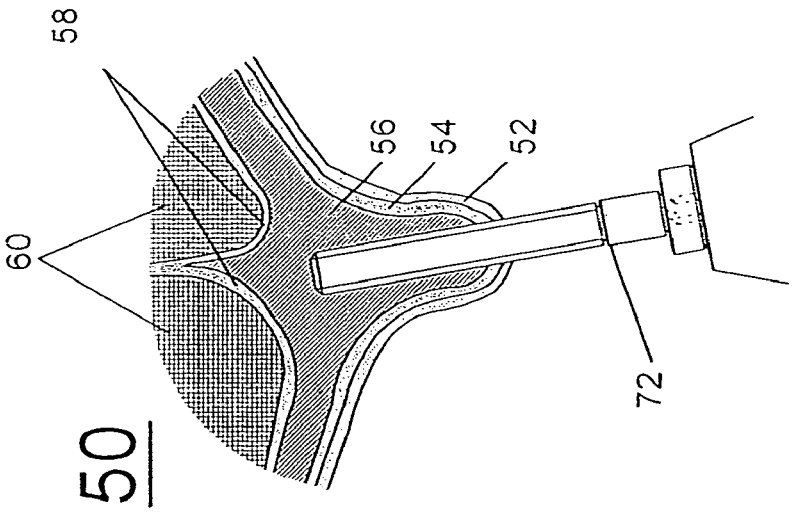
FIG. 3a shows a schematic sectional view a maxilla.
Figure 3B:
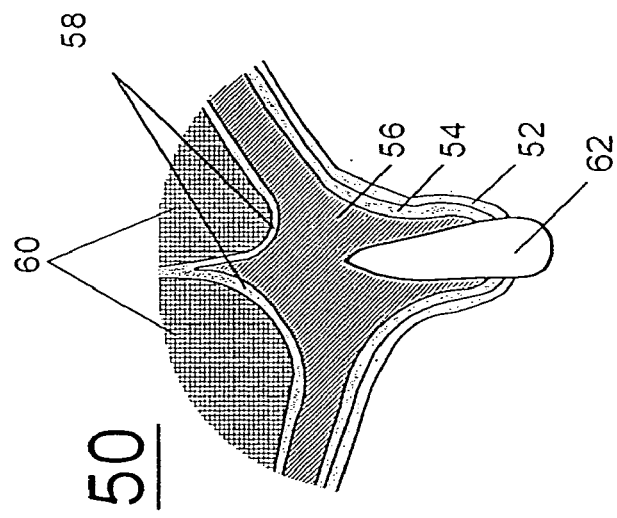
FIG. 3b shows a sectional view of a maxilla after the loss of a tooth.
Figure 4:
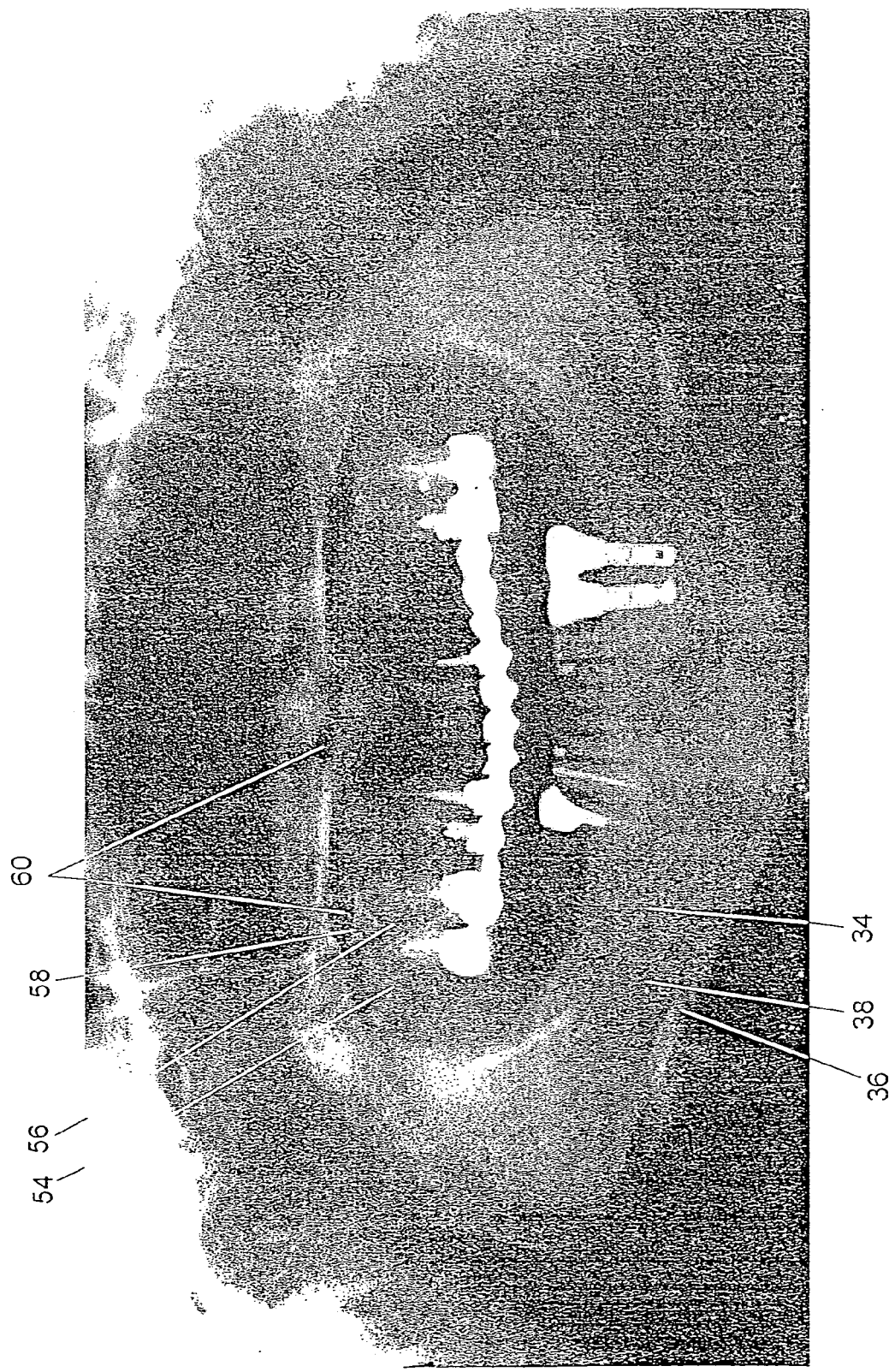
FIG. 4 is an example of a panoramic x-ray image of a mandible and a maxilla.

The principles and operation of systems, methods and devices according to the present invention may be better understood with reference to the drawings and accompanying descriptions.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

Figure 19:
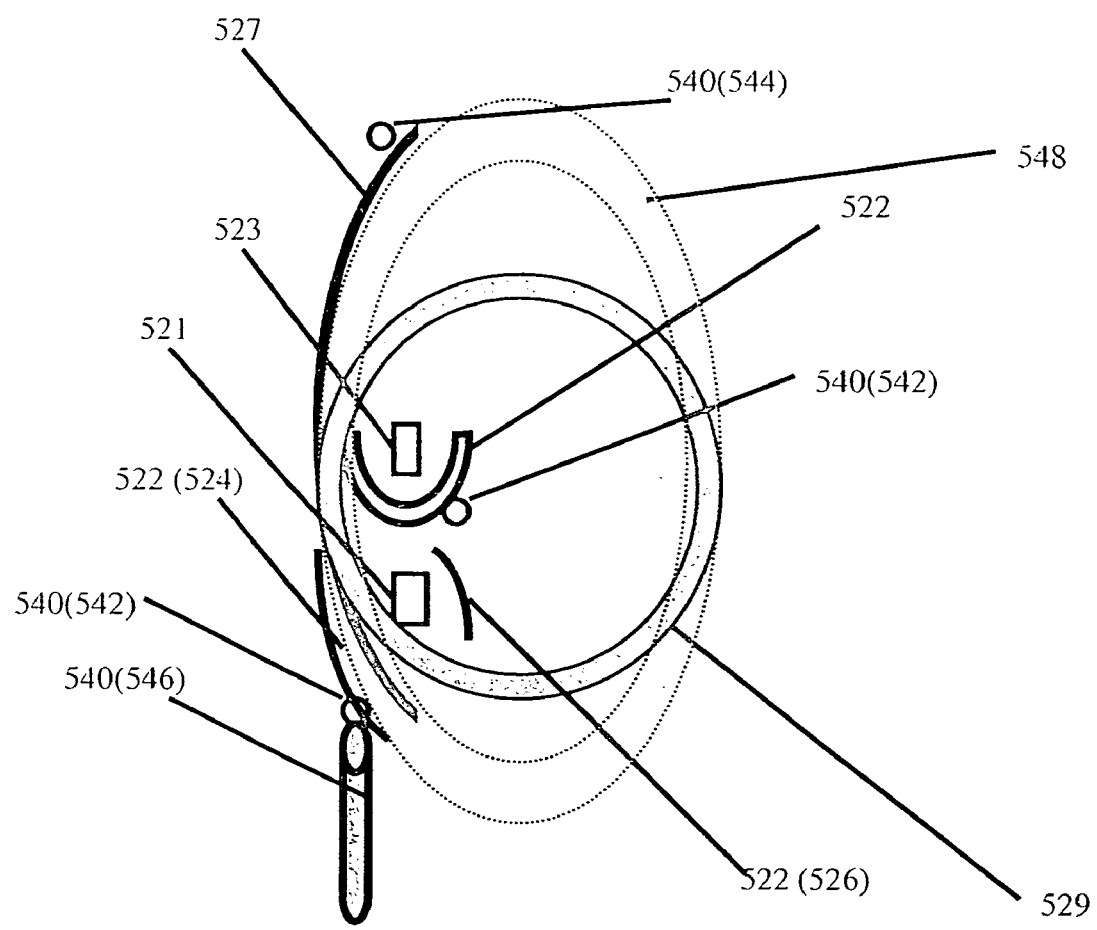
FIG. 19 is a cartoon illustrating positioning of components of various embodiments of a system according to the present invention relative to the jaws and head of a patient.
Figure 20:
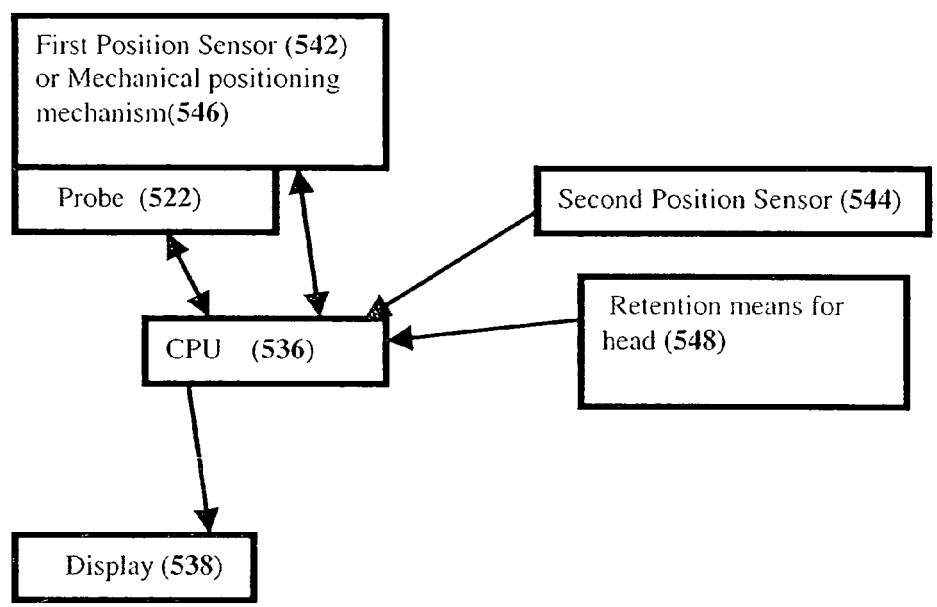
FIG. 20 is a schematic representation of communication between components of various embodiments of a system according to the present invention.
Figure 21:
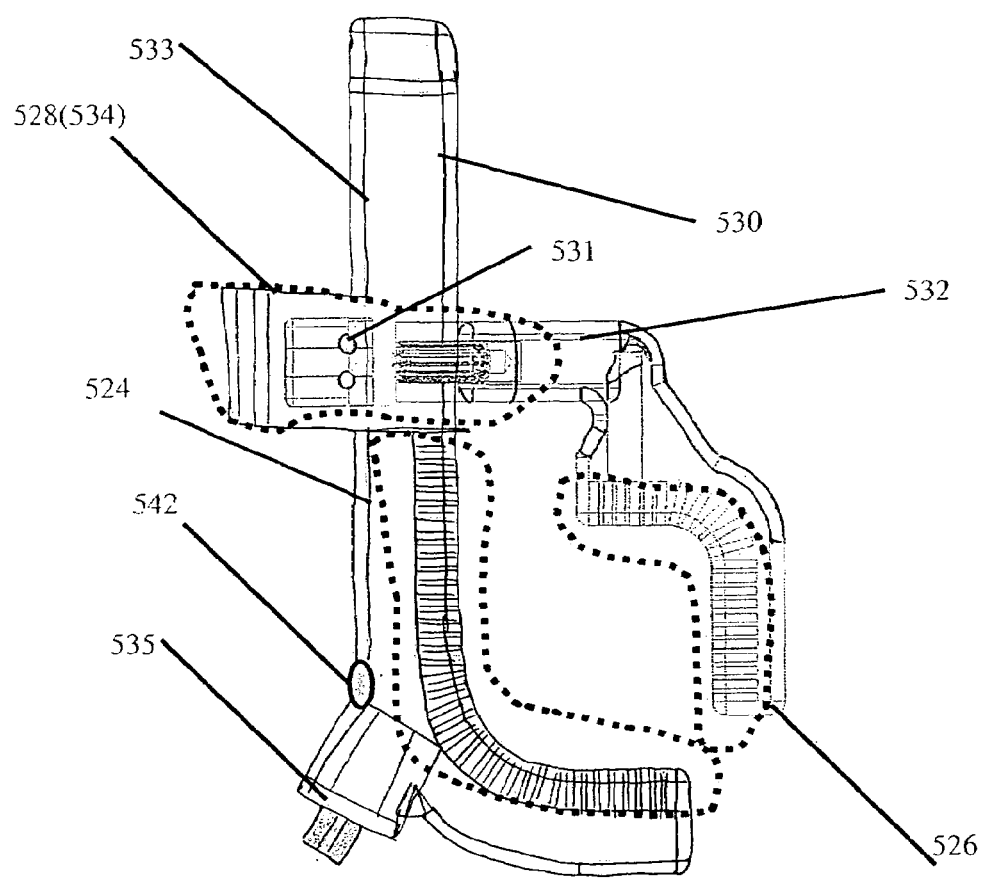
FIG. 21 is a is a cross sectional view of a mandibular probe according to the present invention.

Referring now to the drawings FIGS. 19 and 20 illustrate the arrangement of important operational components of systems 520 according to the present invention with respect to the head 527 and mouth 529 of a patient. The improved ultrasonic imaging system 520 is constructed to facilitate imaging of at least a portion of a jaw. The jaw may be either upper jaw (maxilla) 521 or lower jaw (mandible) 523 which are represented in cross section in FIG. 19 as rectangles for simplicity. System 520 includes a probe 522 which includes at least one array of ultrasonic transducers (e.g. 524 or 526; see also FIGS. 21 and 22). Probe 522 further includes a position locator module 540 designed and constructed to be capable of defining a location of probe 522 in six degrees of freedom and transmitting the definition to a central processing unit (CPU) 536. System 520 further includes-CPU 536. CPU 536 is capable of, by virtue of design and configuration performing several functions. These functions include, but are not limited to, receiving from the probe digital data from each of the ultrasonic transducers arrays (e.g. 524 or 526), further receiving position locator module 540 a location of probe 522 and transforming the digital data into an image of the at least a portion of the jaw 521 or 523. CPU 536 displays the image on a display 538 such as, for example a CRT, LCD, or Plasma screen display. The displayed image may be color or greyscale according to various preferred embodiments of the invention. CPU 536 is preferably further equipped with at least one input device such as a keyboard, touchscreen, mouse, trackpad/ball or microphone. The input device permits an operator to, for example, manipulate the image on display 538 (e.g. control size, brightness or contrast) and/or to control components of system 520 such as transducers 524 and/or 526 of probe 522 and/or mechanical positioning mechanism 546 of probe 522.

The displayed image is preferably three dimensional image prepared by CPU assisted assembly of a series of planar images acquired by probe 522. The image preferably depicts features such as bones, teeth and nerve canals (see FIGS. 24a,b,c and d.) FIG. 24d clearly indicates that images acquired by ultrasound are more informative than those acquired by prior art X-ray methods.

According some preferred embodiments of system 520, probe 522 is a mandibular probe designed and constructed to facilitate imaging of at least a portion of a lower jaw 521. The mandibular probe 522 (see FIG. 21) includes a first array 524 of ultrasonic transducers mounted upon a first wand 530. First array 524 of ultrasonic transducers is positionable distal to lower jaw 521 and outside of a mouth 529. Mandibular probe 522 further includes a second array 526 of ultrasonic transducers mounted upon a second wand 532. Second array 526 of ultrasonic transducers is positionable proximal to lower jaw 521 and inside of mouth 529. Mandibular probe 522 further includes at least one connective member 528 (534). The connective member is designed and constructed to connect the first and second wands 530 and 532 one to another and to allow relative positioning thereof. The connective member 528 includes an assembly designed and constructed to attach the first and second wands and facilitate translational motion (534) of the wands with respect to one another. In the pictured embodiment, complementary arcuate teeth 533 and gears 531 are employed to facilitate translational motion (534) of the wands 530 and 532 with respect to one another although any known mechanical, electrical or robotic means might be employed without significantly altering the invention. In the pictured embodiment cable 535 is employed for data transfer to CPU 536 although transfer via microwave, RF or infrared may alleviate the requirement for a physical connection between components of system 520.

According to alternate preferred embodiments of the invention, probe 522 (shown in greater detail in FIGS. 22a and b) is designed and constructed to facilitate imaging of at least a portion of an upper jaw (maxilla; 523) and includes a single curved array 524 of ultrasonic transducers mounted upon a wand 530 which is designed and constructed to be insertable into a mouth 529 of a patient. Transducers 524 are preferably mounted on an inner surface of curved wand 530 which can transverse, or straddle, maxilla 523 at a chosen point. It has been determined that a few standard sizes, preferably 9 or fewer, more preferably 6 or fewer, more preferably 3 or fewer, of maxillary probe 522 can permit imaging of maxilla of virtually all portions of maxilla 523 of virtually all patients. This relieves the requirement for a positioning mechanism 534 employed in the mandibular configuration of probe 522.

According to some preferred embodiments, the position locator module 540 includes at least one first position sensor 542 located on probe 522 and at least one second position sensor 544 located on a head 527 of a subject. In mandibular probe 522 (FIG. 19), first position sensor 542 includes two position sensors, one on each of wands 530 and 532.

Alternately, but also preferably, position locator module 540 includes a first mechanical positioning mechanism 546 designed and constructed to position probe 522 and a retention means 548 (represented as a grey oval in FIG. 19) designed and constructed to engage and retain a head of a subject in a known position which CPU 536 can employ as a basis for calculation. Retention means 548 may be of the type commonly employed during ophthalmologic examinations and may optionally be equipped with a second positioning mechanism (not shown). Typically, a patient presses forehead and chin into retention means 548 during the examination. As an example, a mini BIRd positioner (Ascension Technology Corporation) might be employed. Incorporation of such a commercially available device into the contect of the present invention will be readily accomplished by one of ordinary skill in the art.

Figure 25:
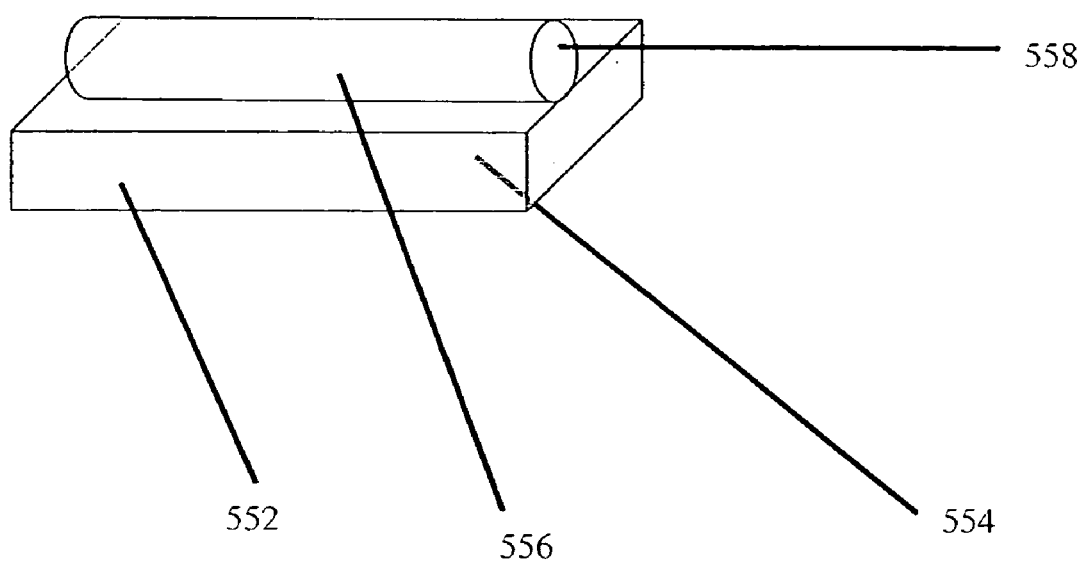
FIG. 25 is a perspective view one embodiment of a coupling cushion according to the present invention.

Preferably system 520 further includes an ultrasonic coupling cushion 550 (see FIG. 25). Cushion 550 includes an elastic container 552 capable of retaining a coupling medium 554 therein. Elastic container 552 is designed and constructed to be insertable in a mouth of a subject and will typically have a thickness of 2 to 20 mm. Cushion 550 is positioned between probe 522 and jaw 521 or 523. Cushion 550 obviates the need for conductive fluid or gel inside the mouth so that an image may be acquired without requiring the patient to spit or rinse. Further, cushion 550 may be used between probe 522 the face in the case of a mandibular probe which has one array of transducers 524 located outside mouth 529. This eliminates the need to apply conductive gel to the face which may be especially important to patients with beards. Additional details of the configuration of cushion 550 are provided hereinbelow.

Figure 23:
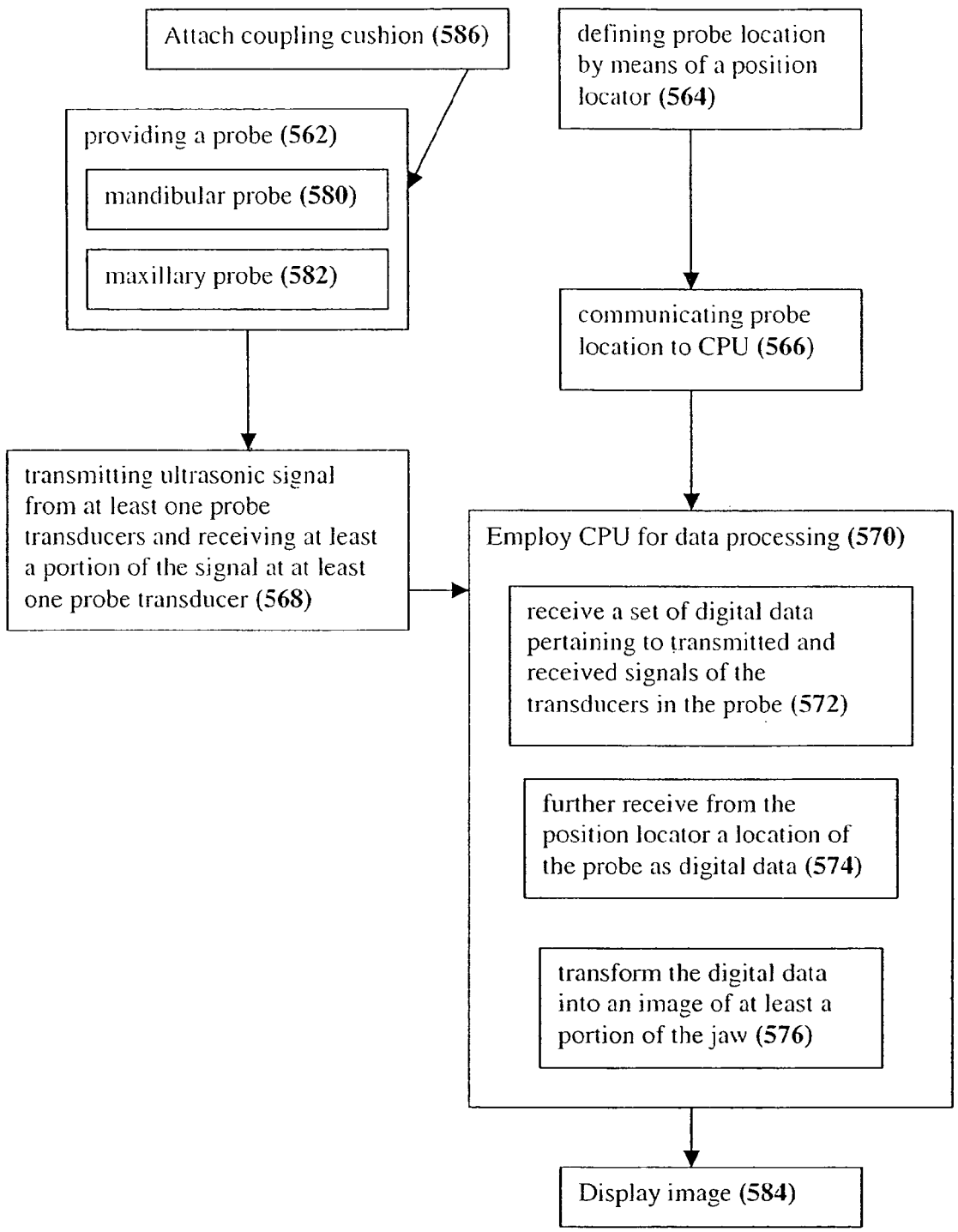
FIG. 23 is a flow diagram illustrating events associated with performance of methods according to the present invention.

The invention is further embodied by a method 560 (FIG. 23) of producing an ultrasonic image of at least a portion jaw 521 or 523. Method 560 includes providing 562 a probe 522. According to various embodiments of the invention, this may include providing 530 a mandibular probe 522 as detailed hereinabove or providing 582 a maxillary probe 522 as detailed hereinabove. In any case, probe 522 includes at least one array of ultrasonic transducers 524 and/or 526.

Method 560 further includes defining 564 a location of probe 522 by means of position locator module 540 as detailed hereinabove. Method 560 further includes communicating 566 the location to CPU 536. Method 560 further includes transmitting 568 an ultrasonic signal from at least one of the transducers and receiving at least a portion of the ultrasonic signal at least one of the transducers. Method 560 further includes employing CPU 536 for data processing. CPU 536 serves to receive 572 a set of digital data pertaining to the transmitting and receiving performed by the transducers in arrays 524; 526 of probe 522. CPU 536 further serves to receive 574 from position locator 540 a location the probe 522. CPU 536 further serves to transform the digital data into an image of the at least a portion of jaw 521 or 523. Preferably the image is a three dimensional image. Preferably, method 560 further includes attaching coupling cushion 550 to at least a portion of probe 522.

The present invention is further embodied by ultrasonic coupling cushion 550 (FIG. 25) which includes elastic container 552 capable of retaining coupling medium 554. Elastic container 552 is designed and constructed to be insertable in a mouth of a subject. Preferably, container 552 has a thickness of 1 to 20 mm and an area only slightly larger than that occupied by array of transducers 524 or 526. Preferably coupling cushion 550 further coupling medium 554 which may be, for example, water, an aqueous solution, a gel or a polymer solution.

Preferably elastic container 552 further includes attachment device 556 designed and constricted to engage and retain at least a portion of probe 522. FIG. 22b illustrates use of two attachment devices 556 (dotted lines) to position container 552 probe 522. Attachment device 556 may be, for example a sleeve, a pocket or series of loops. Attachment device 556 includes at least one hole 558 to accept at least a portion of probe 522. Attachment device 556 may be integrally formed with, or attached to, container 552. During use, array of transducers 526 preferably resides in attachment device 556 ultrasonic signals (whether transmitted or received) must pass through elastic container 552 and coupling medium 554 contained therein. Cushion 550 is gently pressed against jaw 521 or 523 during use. This may be accomplished by correct positioning of probe 522 with respect to jaw 521 or 523. According to some embodiments of the invention, valve 553 allows filling of container 552 with coupling medium 554.

Figure 24A:
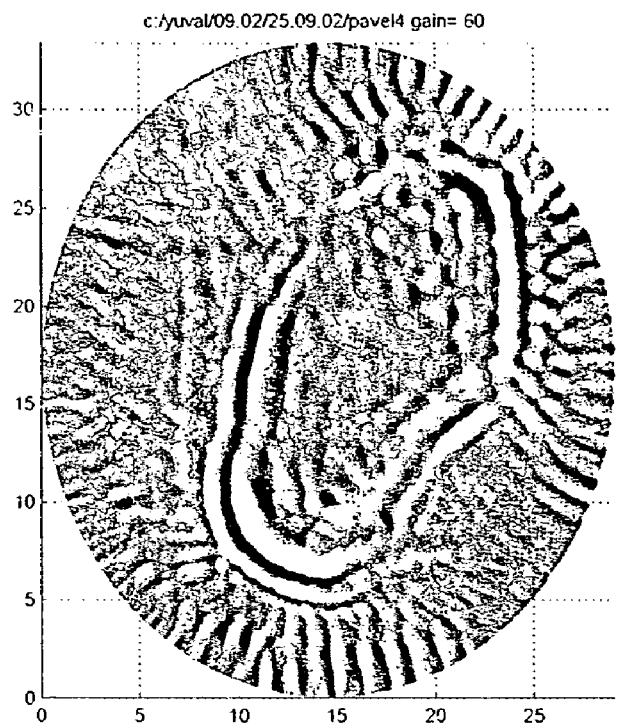
FIGS. 24a, 24b and 24c illustrate sample image outputs of portions of a jaw according to various embodiments of the present invention.

FIGS. 24a, b, c and d illustrate images produced according to various preferred embodiments of the invention. Different images are produced by altering the configuration of CPU 536 and the way in which arrays of transducers 524 (and optionally 526) are operated. A brief, non limiting, explanation of several common imaging technologies suited for use in the context of the present invention is provided Synthetic Aperture Focusing Technique (SAFT)

A synthetic aperture (SA) image, synthesized from reflections collected at both Outside array 524 and Inside array 526 allows depiction of the contour of the bone based on the "first reflection", i.e. the bounding reflection line. The image can also reveal reflectors inside the bone such as the mandibular canal, root canals, or implants. FIG. 24a is an example of an image produced using SAFT.

SAFT+Contour Detection

Figure 24B:
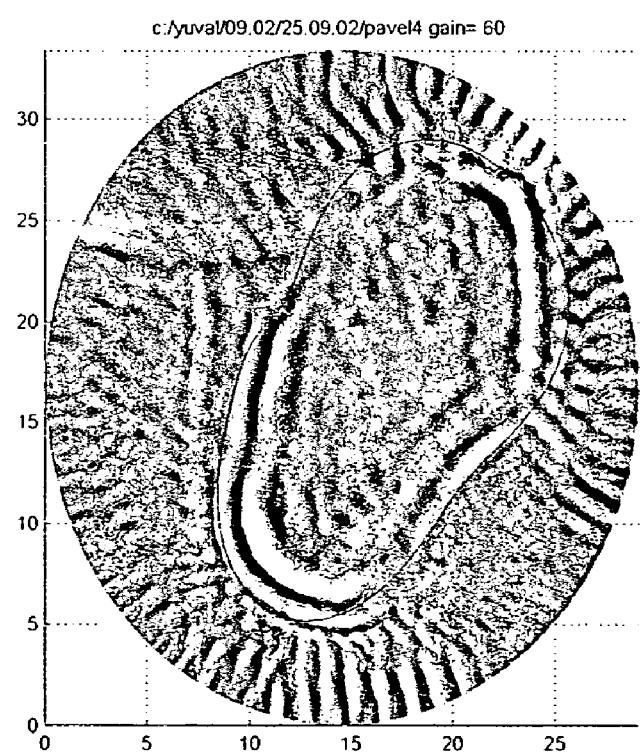

The contour of the bone is computed from the SA image rid, given on polar coordinates C and θ. First a matching filter is used to find points along the bone surface, and second a Fourier polynomial is fitted to the points in an iterative optimization. An improved image results. FIG. 24b is an example of an image produced using SAFT+Contour Detection.

Computerized Tomography (CT)

Computerized Tomography (CT) of Time Of Flight (TOF) allows computing the sound velocity in jawbone 521 or 523. In order to increase the penetration energy CPU 536 employs a scan program which uses several adjacent emitters (usually 2 or 3) for each A-scan. The emitters are electronically focused using phased al-ray electronics. All available scans in through transmission mode are used for solution of the inverse problem.

For Each A-scan the TOF is detected from the first signal with amplitude larger than the noise threshold value. If this TOF is smaller than the TOF calculated for signals passing in water, then the measurement is valid for the tomography calculation.

Figure 24C:
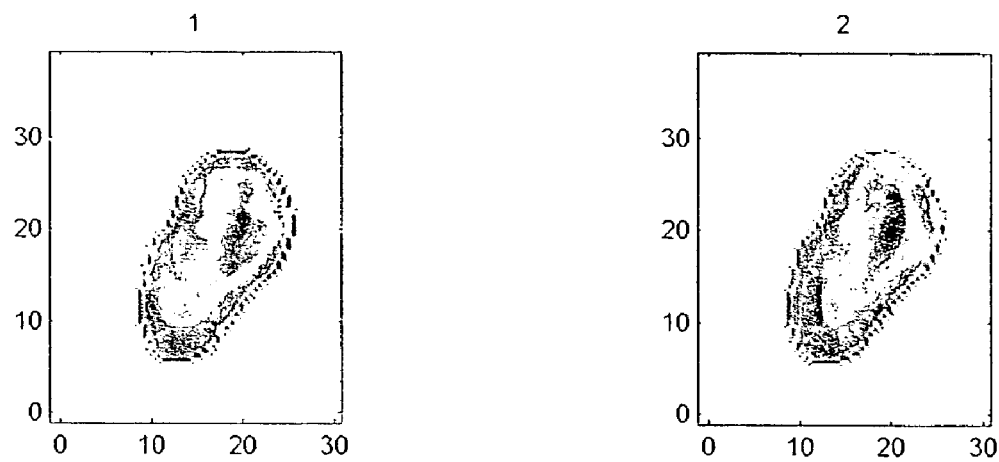
Figure 24D:
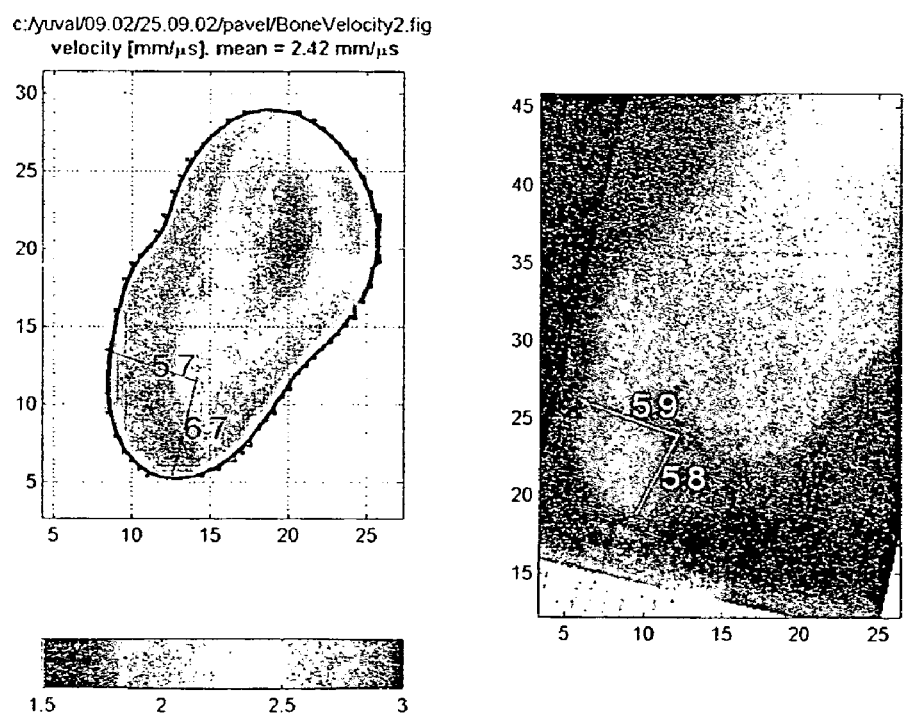
FIG. 24d compares an image produced by the present invention to an image of the same object produced using X-ray technology.

The solution takes into account the contour of the bone, thus reducing the number of image pixels to be resolved, i.e. the degrees of freedom. The method of solution is iterative in two steps. In the first step the radiation is assumed to propagate in straight lines, while in the second step the propagation line is corrected for the differences in the sound velocity in bone that were calculated in the first step. FIG. 24c shows the results of the first step oil the loft (1), and the second step on the right (2). The correction method has two advantages over straight-line tomography. First, it results in more homogeneous areas, and second, the location of objects such as the canal is more correct.

Red color corresponds to high velocity (3 mm/µs), and Blue corresponds to low velocity (1.5 mm/ps as the sound velocity in water). In compact bone the velocities are ~2.5-3.0 mm/µs while in trabecular bone the velocities are ~1.5-2.0 mm/µs. Therefore the velocity image allows differentiating between the cortical and trabecular bones. Also, the nerve canal, filled with "water", can be noticed. FIG. 24d shows the resulting TOF tomography image in comparison with an image produced by X-ray mechanical tomography in the same location for the same patient The present invention discloses a method and apparatus for non-invasive ultrasonic imaging of hard tissue.

Figure 6:
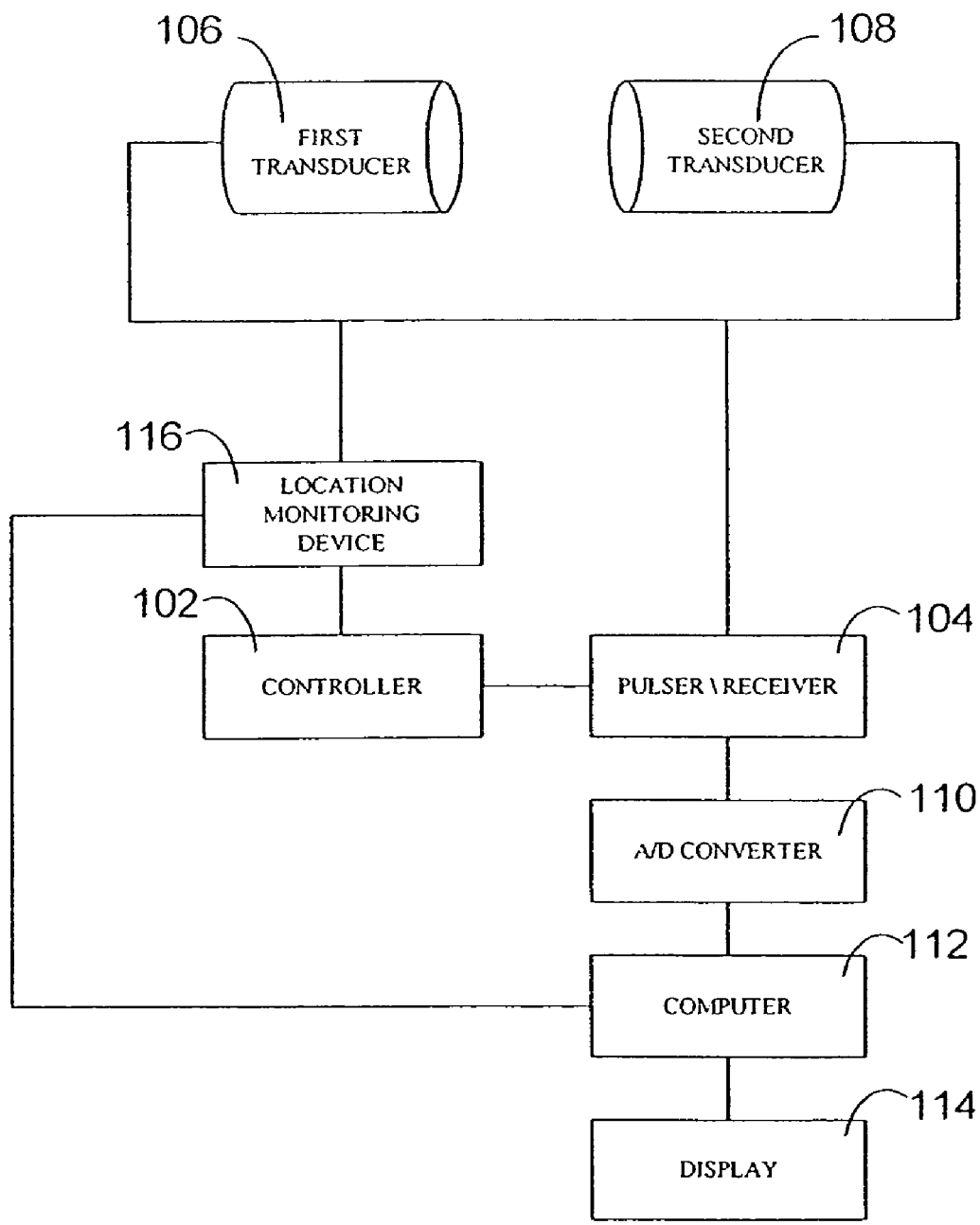
FIG. 6 illustrates a preferred embodiment apparatus of the present invention.

Referring now to FIG. 6, a preferred embodiment of the present invention, designated 100, will be described. Apparatus 100 is an apparatus for non-invasive ultrasonic imaging of hard tissue. Apparatus 100 comprises a controller 102 coupled to a pulser\receiver 104 and to a location monitoring device 116. Pulser\receiver 104 is coupled to a first transducer 106, to a second transducer 108 and to an analog-to-digital converter (ADC) 110. ADC 110 is coupled to a computer 112, which is coupled to a display device 114. Location monitoring device 116 is coupled to first transducer 106, to second transducer 108, and to computer 112.

Referring now to FIG. 7, the method of operation of apparatus 100 will be described. Apparatus 100 operates according to a through-transmission method, as follows. A user couples first transducer 106 to an initial location on a surface of an organ being examined, for example, on a first surface 32 of a mandible 30. First surface 32 can be, for example, a surface inside the mouth cavity, such as the buccal or lingual gum surface of the jaw, or a surface outside the mouth cavity, such as the surface of the cheek or the chin. Alternatively, in case the jawbone is exposed (e.g. by raising the mucoperiosteal flap) first transducer 106 can be coupled directly to a bone surface of the jaw. In FIG. 7, for example, first surface 32 is a toothless buccal gum surface, although the same procedure can be performed on a surface under which a tooth is present.

The user couples second transducer 108 to an initial location on a surface opposite to transducer 106. In FIG. 7, for example, second transducer 108 is coupled to a second surface 32' of mandible 30, which is opposite to first surface 32 to which first transducer 106 is coupled. If, for example, first surface 32 is the buccal gum surface of mandible 30, then second surface 32' can be the lingual surface thereof; if first surface 32 is the lingual surface of mandible 30, then second surface 32' can be, for example, the buccal gum surface or cheek surface opposite thereto. Like first transducer 106, second transducer 108 can be coupled directly to a bone surface of the jaw, in case the jawbone is exposed.

In order to improve receipt by second transducer 108 of ultrasonic signals emitted by first transducer 106, the user preferably aligns the two transducers so that they face one another on a predetermined common axis $CX_{106}$. In order to further improve penetration of ultrasound signals into mandible 30, the user applies a coupling material 74 between first transducer 106 and first surface 32, and between second transducer 108 and second surface 32'. In some cases, the fluids naturally present in the mouth of the patient (e.g. saliva) will be sufficient to serve as coupling material 74. In other cases, the user can use another material for coupling, for example, a non-toxic ultrasound coupling gel.

When the transducers are properly coupled, the user starts the operation of apparatus 100 using controller 102. The controller commands location monitoring device 116 to determine the initial location of first transducer 106 and the initial location of second transducer 108. Device 116 determines the initial locations using a conventional measuring method and sends the results to computer 112. The controller further commands pulser\receiver 104 to generate electrical pulses and to send them to first transducer 106. First transducer 106 converts the electrical pulses to ultrasonic pulses and emits them toward first surface 32. The emitted ultrasonic pulses partially penetrate first surface 32 via coupling material 74. Some of the penetrating ultrasonic pulses then travel inside mandible 30 through cortical bone layer 34, trabecular bone 36, opposite cortical bone layer 34' and second. (opposite) surface 32', eventually reaching second transducer 108 via coupling material 74. Second transducer 108 receives ultrasonic pulses which propagated through mandible 30, converts them into analog electrical pulses and sends the electrical pulses to ADC 110 via pulser\receiver 104. The ADC samples the electrical pulses which represent the received pulses and sends these samples to computer 112. The computer records, as a first set of results, the samples which represent the received pulses along with the initial location of the emitting transducer and the initial location of the receiving transducer.

Figure 8C:
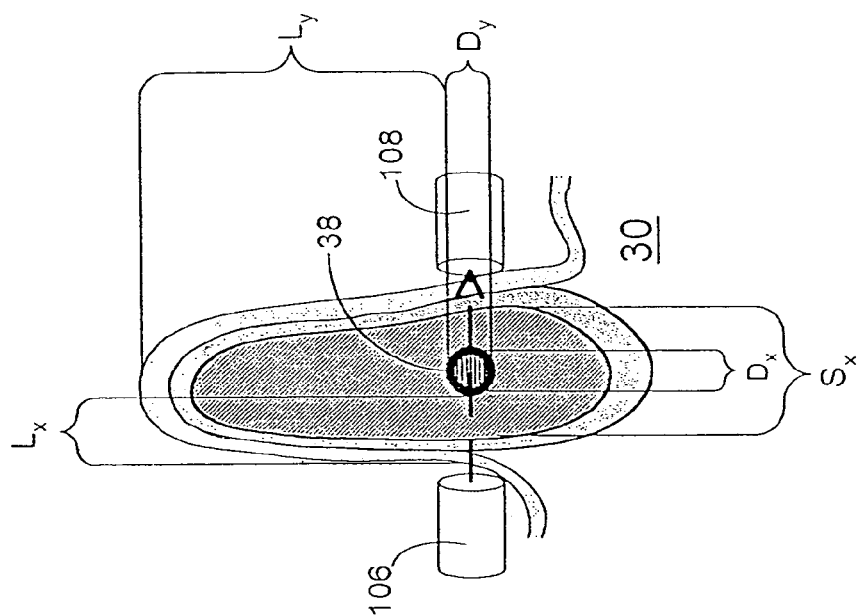
FIGS. 8a-8c illustrate an example of a vertical, parallel scanning movement.
Figure 8B:
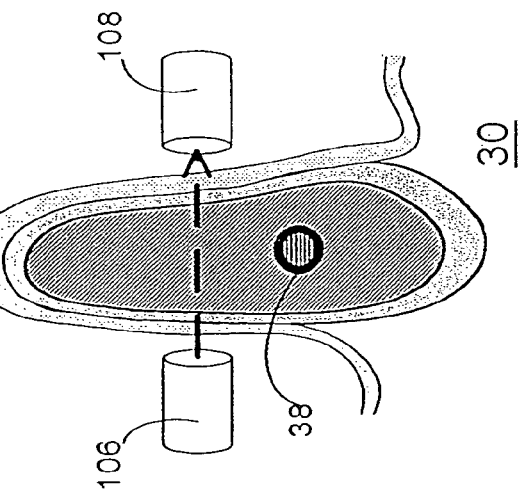
Figure 8A:
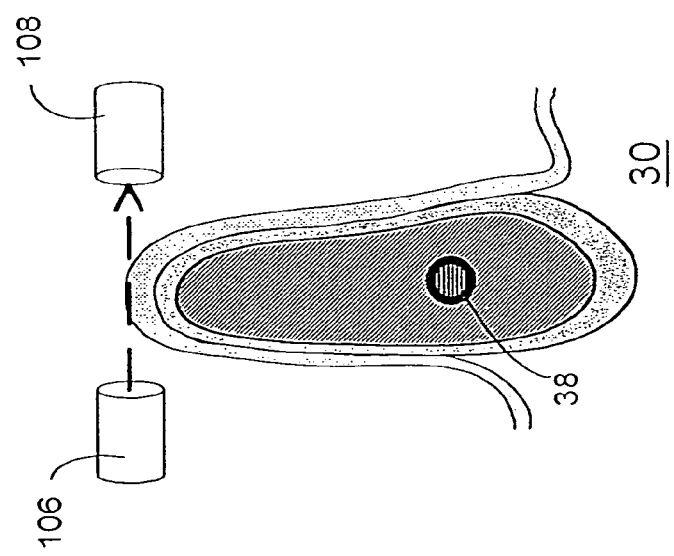
Figure 9A:
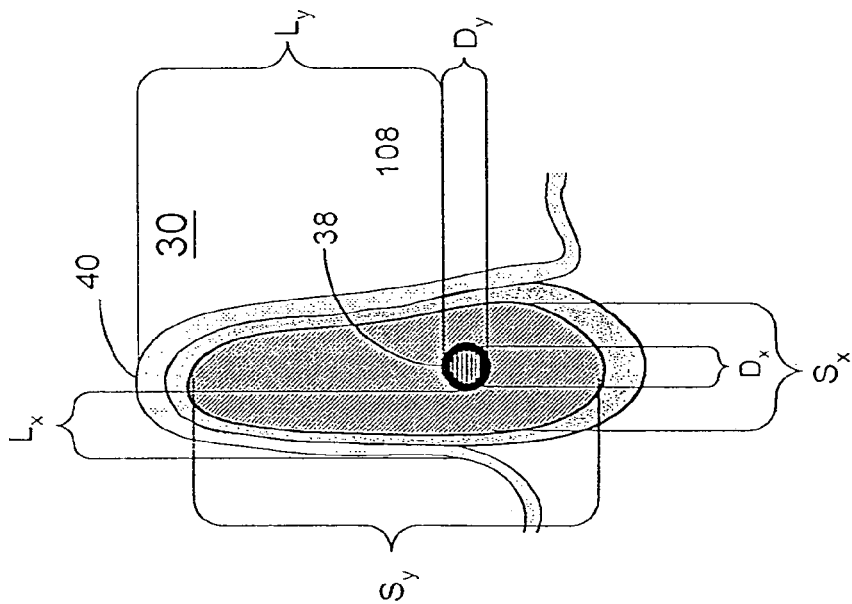
FIGS. 9a-9c illustrate an example of a horizontal, parallel scanning movement.
Figure 9B:
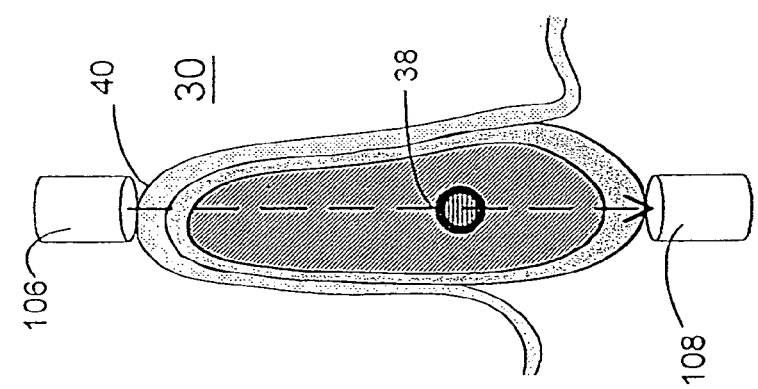

The user scans mandible 30, for example, by moving first transducer 106 along first surface 32 whilst also moving second transducer 108 along second surface 32' in parallel to the first transducer. FIGS. 8a-8c illustrate an example of a vertical, parallel scanning movement. FIG. 8a shows the initial locations of transducers 106 and 108 which are relatively far from mandibular canal 38. FIG. 8b shows the locations of the two transducers after having been moved, in parallel, approximately halfway closer to mandibular canal 38. FIG. 8c shows the locations of the two transducers after having been moved further in parallel, so that mandibular canal 38 lies on the ultrasonic travel path (depicted as a broken-line arrow) between the two transducers. FIGS. 9a-9b illustrate an example of a horizontal, parallel scanning movement. First transducer 106 is coupled to alveolar ridge 40 of mandible 30 and second transducer 108 is coupled to the floor of the mandible, opposite to and facing first transducer 106. FIG. 9a shows the initial locations of the transducers. The transducers are initially placed so that the travel path (depicted as a broken-line arrow) of ultrasonic pulses does not pass through mandibular canal 38. FIG. 9b shows the location of the two transducers after having been moved, in parallel, toward the middle of the jaw, so that mandibular canal 38 lies on the path between first transducer 106 and second transducer 108.

Figure 9C:
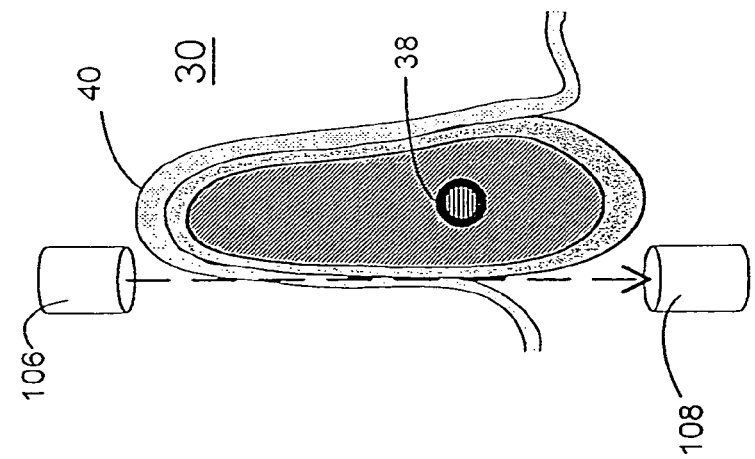

Alternatively, instead of a parallel scanning motion (FIGS. 8 and 9), the user may also scan mandible 30 by moving only one transducer whilst the other transducer remains stationary, by moving the two transducers; in opposite directions or any other desired scanning pattern. Apparatus 100 can further be equipped with automatic mechanical scanning means, for example, a slidable mount to which one or both of the transducers are attached and which is programmed to execute a desired scanning pattern. Alternatively, apparatus 100 can be equipped with electronic scanning means, for example, an array of transducers instead or in addition to transducer 106 and\or transducer 108.

During the scanning process, ADC 110 samples the ultrasonic pulses received at each new location of the transducers, and computer 112 keeps recording sets of samples along with corresponding locations of the transducers. Computer 112 is further programmed to determine certain physical characteristics of the hard tissue being examined, based on an analysis of the recorded sets.

When ultrasonic pulses travel inside hard tissue, they often pass through layers, areas and\or internal structures which possess different acoustic properties.

The difference between acoustic properties of an internal structure within hard tissue on one hand, and acoustic properties of the proximate surroundings of the internal structure on the other hand, makes it possible for apparatus 100 to detect, locate, measure and image such an internal structure within hard tissue. For example, when the hard tissue being examined by apparatus 100 is a mandible, penetrating ultrasonic pulses will sometimes propagate through mandibular canal 38 on their path from first transducer 106 to second transducer 108. This will be the case, for example, if mandibular canal 38 lies on the path between the two transducers (as illustrated in FIG. 8c). According to the teachings of the present invention, mandibular canal 38 possesses different acoustic properties than trabecular 36 and cortical bone 34. For example, since the mandibular canal is typically filled with fluids, it will sometimes be characterized by lower ultrasonic attenuation than cortical and trabecular bone. In other cases, the geometry of the mandibular canal may actually cause penetrating ultrasonic pulses to scatter, eventually causing higher attenuation than cortical and trabecular bone. The present invention therefore teaches that when, during the scanning process, mandibular canal 38 is situated on the path between first transducer 106 and second transducer 108 (e.g. FIGS. 8c and 9b), consequently computer 112 will be able to detect a local change (increase or decrease) in amplitude of the received and sampled pulses.

Hence, it is a particular feature of apparatus 100 that it detects and locates an internal structure within hard tissue (e.g. the mandibular canal in a mandible), by detecting a local change in the amplitude of penetrating ultrasonic pulses. When computer 112 detects such a local change in the amplitude, it will notify the user (e.g. by issuing an indication on display 114) that an internal structure lies on the ultrasonic travel path between first transducer 106 and second transducer 108.

It is another particular feature of apparatus 100 that it Can measure the depth of an internal structure within hard tissue, such as the depth of the mandibular canal in a mandible, based on amplitude measurements. By "depth" is meant the distance from a surface of the organ being examined to the internal structure of interest. For purposes of illustration hereunder, horizontal depth $L_x$ means the horizontal distance from surface 32 to the nearest border of mandibular canal 38, and vertical depth $L_y$ means the vertical distance from alveolar ridge 40 to the nearest border of mandibular canal 38 (see FIGS. 8c and 9c). The method of operation of apparatus 100 in measuring the depth of an internal structure within the hard tissue, for example, the depth of mandibular canal 38 within mandible 30, is as follows. The transducers scan mandible 30 according to the method described heretofore. As soon as computer 112 first detects a characteristic change in the amplitude of penetrating ultrasonic pulses, it means that the pulses have first met mandibular canal 38 on their path from first transducer 106 to second transducer 108. Since the computer receives from location monitoring device 116 the location of the transducers at any given moment, the computer can therefore calculate the depth of mandibular canal as follows. In case of vertical scanning (FIGS. 8a-8c), vertical depth $L_y$ will be calculated as the vertical distance from alveolar ridge 40 to the location of the transducers which first introduced a characteristic amplitude change. Similarly, in case of horizontal scanning (FIGS. 9a-9c), horizontal depth $L_x$ will be calculated as the horizontal distance from surface 32 to the location of the first characteristic amplitude change. The measured depth will then be displayed on display 114.

Figure 5A:
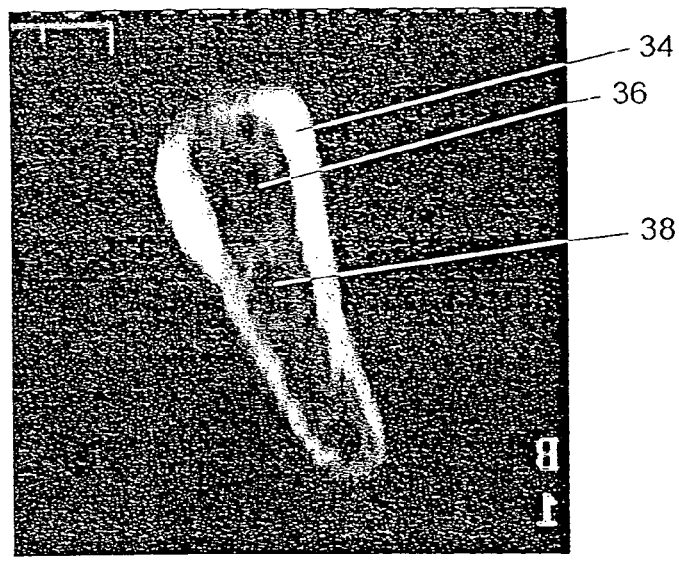
FIG. 5a is an example of a sectional CT image of a toothless mandible.
Figure 5B:
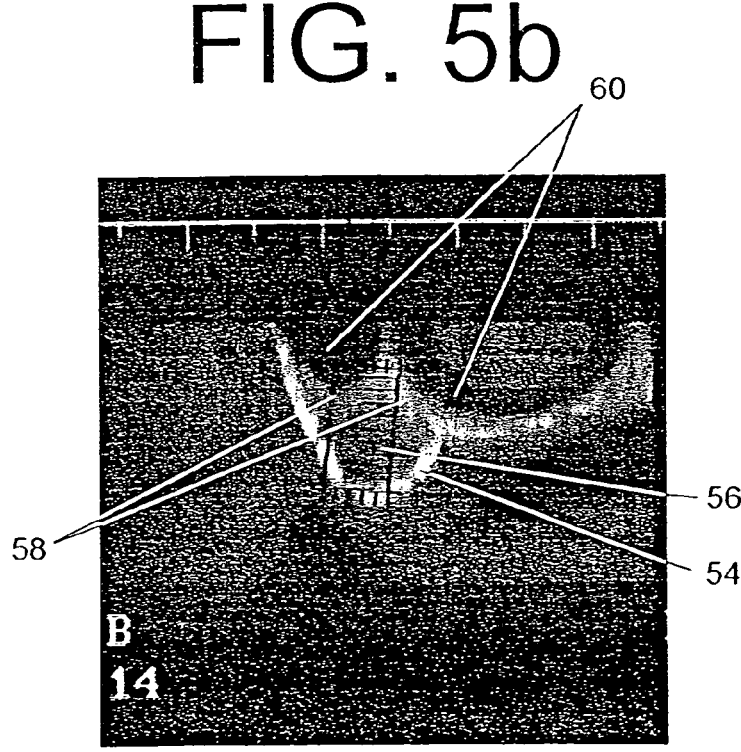
FIG. 5b is all example of a sectional CT image of a toothless maxilla.

It is yet another particular feature of apparatus 100 that it can measure the diameter of an internal structure of interest within hard tissue, for example, the diameter of mandibular canal 38 within mandible 30, based on amplitude measurements. The borders of mandibular canal 38 are usually elliptic rather than round (see FIG. 5a), and therefore the diameter may differ depending on the direction from which it is measured. For purposes of illustration hereunder, horizontal diameter $D_x$ means the diameter which lies approximately on the horizontal axis of the jaw, and vertical diameter $D_y$ means the diameter which lies approximately on the vertical axis thereof (see FIGS. 8c and 9c). The method of operation of apparatus 100 in measuring the diameter of an internal structure within hard tissue, for example, the diameter of mandibular canal 38 in mandible 30, is as follows. The transducers scan mandible 30 according to the method described heretofore. When measuring horizontal diameter $D_x$ horizontal scanning (FIG. 9) will be performed, and when measuring vertical diameter $D_y$ vertical scanning (FIG. 8) will be performed. As soon as computer 112 first detects a characteristic change in the amplitude of penetrating ultrasonic pulses, it means that the pulses have first met mandibular canal 38 on their path from first transducer 106 to second transducer 108. Subsequently, when amplitude returns to its level prior to the characteristic change, it means that the penetrating ultrasonic pulses no longer pass through mandibular canal 38. Computer 112 then calculates and displays the diameter of mandibular canal 38 based on the detected borders of the canal and on location information supplied by location monitoring device 116.

It is yet another particular feature of apparatus 100 that it can detect and locate an internal structure within hard tissue, for example mandibular canal 38 within mandible 30, based on spectral function analysis. Transducers 106 and 108 scan mandible 30, and ADC 110 sends to computer 112 samples of the received ultrasonic pulses, all as explained hereinabove. Computer 112 processes the samples and produces, for each pair of locations of the transducers, a spectral function representing ultrasonic pulses emitted from and received at those locations. The spectral functions can be produced, for example, using a known Fast Fourier Transform (FFT) algorithm. The computer records, for each given location of the transducers, a set containing the spectral function of the received ultrasonic pulses along with the corresponding location of the transducers. Computer 112 can then analyze various characteristics of the spectral functions of the received ultrasonic pulses to determine the location of an internal structure within the hard tissue being examined. For example, it is known in the art that if an ultrasonic signal propagates through a medium which causes attenuation, the energy of the signal will be concentrated in a lower frequency range than in the original signal In general, a higher level of attenuation will cause a greater frequency shift. As mentioned heretofore, the present invention teaches that mandibular canal 38 often causes a different level of attenuation than cortical 34 and trabecular bone 36 around it. It therefore follows that the frequency spectrum of ultrasonic pulses received by second transducer 108 after having traversed mandible 30 via mandibular canal 38 (FIGS. 8c and 9b), will often be shifted compared to the frequency spectrum of similar ultrasonic pulses which did not travel through the mandibular canal.

FIG. 10 illustrates an example of three spectral functions of the same ultrasonic signal: a first spectral function 210 represents the ultrasonic signal as it is originally emitted into a jaw; a second spectral function 212 represents the same ultrasonic signal as received after having propagated mainly through the trabecular bone of the jaw (FIGS. 8a, 8b or 9a); and a third spectral function 214 representing the same ultrasonic signal as received after having traveled partly through trabecular bone and partly through the mandibular canal (FIG. 8c or 9b). In this example, the frequencies of peak amplitudes $P_{212}$ and $P_{214}$ of spectral functions 212 and 214 (i.e. of the attenuated received signals) are lower than the frequency of peak amplitude $P_{210}$ of spectral function 210 (i.e. of the originally emitted signal). Furthermore, the example illustrates that the frequency of peak amplitude $P_{214}$ of ultrasonic pulses which traveled partly through mandibular canal is higher than the frequency of peak amplitude $P_{212}$ of ultrasonic pulses which traveled mainly through trabecular bone. Hence, when computer 112 detects a characteristic frequency shift in the spectral function of received ultrasonic pulses, it will notify the user (e.g. by issuing an indication on display 114) that an internal structure lies on the ultrasonic travel path between first transducer 106 and second transducer 108.

It is yet another particular feature of apparatus 100 that it can detect and locate an internal structure within hard tissue, based on artificially amplified characteristics of the received pulses, such characteristics being indicative of the internal structure. In some cases, the effect of the internal structure of interest on ultrasonic pulses traveling through it, may not be easily distinguishable from the effect of the surrounding area. This is the case, for example, when the level of attenuation inside mandibular canal 38 is nearly equal to the level of attenuation inside cortical 34 and trabecular bone 36. In such cases, computer 112 may perform further manipulations on the samples which represent the received ultrasonic pulses, in order to amplify certain characteristics which enable detecting the internal structure.

According to this method, after computer 112 obtains spectral functions of ultrasonic pulses received in various locations across mandible 30 (as explained hereinabove), the computer processes the recorded spectral functions to determine a discrete representative value for each spectral function. Such a representative value can be, for example, the minimal, maximal, average or root mean square (RMS) amplitude of each spectral function, or the total sum of all amplitudes in each spectral function, or any other predetermined representation criterion. As a result, the computer obtains and records a first array of representative values as a function of the locations of the transducers across mandible 30. Following, the computer analyzes the first array, in order to detect a distinct local variability in the representative values. In case such distinct local variability is found, the computer can conclude and notify the user (e.g. on display 114) that the internal structure of interest is situated in the locations corresponding, to the locally varying representative values. If no such distinct local variability is detected, the computer will proceed and obtain a second array of representative values, which is based on a different representation criterion than that of the first array. If the first array is, for example, an array of the total sum of amplitudes, then the second array can be, for example, an array of the RMS of amplitudes. The computer analyzes the second array to find a distinct local variability which indicates the presence of the internal structure of interest. If again no such distinct local variability is detected, the computer will perform a predetermined mathematical manipulation on the first and\or second arrays. For example, the computer can divide the first array by the second array to obtain a third, synthetic array of representative values as a function of locations across the mandible. The computer analyzes the third, synthetic array to find a distinct local variability which indicates the presence of the internal structure. Often the synthetic array will be characterized by a distinct local variability, even though the first and second arrays which formed the third array were not so characterized. This is because certain mathematical manipulations may amplify physical effects which indicate the presence of the internal structure of interest. The computer may repeat the above procedure a desired number of repetitions.

It is yet another particular feature of apparatus 100 that it enables calculating the diameter of an internal structure within hard tissue, based on analysis of the ratio between the amplitude of received ultrasonic pulses and the attenuation coefficients inside the organ being examined. According to this method, after computer 112 obtains spectral functions of ultrasonic pulses received in various locations across mandible 30 (as explained hereinabove), the computer determines the minimal amplitude $A_1$ of ultrasonic pulses received by second transducer 108 during the scanning process, and the maximal amplitude $A_2$ of such pulses.

As previously taught herein, attenuation in mandibular canal 38 is typically different than in cortical 34 and trabecular bone 36. Where attenuation in the mandibular canal is lower than in cortical and trabecular bone, minimal amplitude $A_1$ will be measured when penetrating ultrasonic pulses do not travel through mandibular canal 38 (FIGS. 8a, 8b or 9a), whereas maximal amplitude $A_2$ will be measured when the pulses travel partly via mandibular canal 38 (FIG. 8c or 9b). Horizontal width $S_x$ of trabecular area 36 is approximately equal to the total horizontal travel distance of ultrasonic pulses (in case of vertical scanning). Similarly, the vertical width $S_y$ is approximately equal to the total vertical travel distance of ultrasonic pulses (in case of horizontal scanning). The attenuation coefficient inside trabecular area 36, designated $\gamma_1$, as well as the attenuation coefficient inside mandibular canal 38 (approximately equal to the attenuation coefficient in water) designated $\gamma_2$, are both measured using conventional means and are fed into computer 112.

It is known in the art that the ratio between the amplitude A of a received ultrasonic signal and the distance S traveled by the ultrasonic signal inside a medium with an attenuation coefficient $\gamma$ can be expressed by the following first equation:

$$A \approx e^{-(\gamma \cdot S)}$$

Hence, the ratio between minimal amplitude $A_1$ and trabecular width $S_x$ can be expressed by the following second equation:

$$A_1 \approx e^{-(\gamma_1 \cdot S_x)}$$

And the ratio between maximal amplitude $A_2$ and diameter $D_x$ of mandibular canal 38 can be expressed by the following third equation:

$$A_2 \approx e^{-(\gamma_1 \cdot (S_x - D_x) + (\gamma_2 \cdot D_x))}$$

If the third equation is divided by the second equation, then the following fourth equation is obtained:

$$\frac{A_2}{A_1} = e^{(\gamma_1 - \gamma_2) \cdot D_x}$$

The above fourth equation can be solved for $D_x$ as expressed by the following fifth equation:

$$D_x = \frac{\left(\log \frac{A_2}{A_1}\right)}{(\gamma_1 - \gamma_2)}$$

Thus, having acquired minimal and maximal amplitude measurements $A_1$ and $A_2$ and attenuation coefficients $\gamma_1$ and $\gamma_2$, computer 112 calculates and displays on display 114 horizontal diameter $D_x$ of mandibular canal 38, using the above fifth equation. Vertical diameter $D_y$ can be measured in a similar manner, based on minimal and maximal amplitudes $A_1$ and $A_2$ measured vertically.

It is yet another particular feature of apparatus 100 that it can detect and locate an internal structure within hard tissue (e.g. signal and\or nasal cavities in a maxilla), based on analysis of the ratio between the travel distance and attenuation of ultrasonic pulses within the hard tissue. Referring now to FIG. 15, this method will now be described. As explained hereinabove, transducers 106 and 108 are coupled using coupling material 74 to opposite surfaces of the organ being examined whilst facing each other. For example, in FIG. 15 first transducer 106 is coupled to a first surface 52 of a maxilla 50, and second transducer 108 is coupled to a second surface 52' thereof. In order to ensure that the transducers are facing each other (e.g. when the surface to which first transducer 106 is coupled is not parallel to the surface to which second transducer 108 is coupled), angular transducers may be used. When the transducers are properly coupled, the user starts the operation of apparatus 100 using controller 102. The controller commands location monitoring device 116 to determine the initial locations of the transducers, and to further determine the travel distance TD of ultrasonic pulses inside maxilla 50. Location monitoring device 116 determines the abovementioned factors Using conventional measuring means and sends the measurements to computer 112. Controller 102 further commands pulse\receiver 104 to operate electrical pulses and to send them to first transducer 106 and to ADC 110. First transducer 106 converts the electrical pulses to ultrasonic pulses and emits them toward first surface 52. ADC 110 samples the electrical pulses which represent the emitted pulses and sends these samples to computer 112. The emitted ultrasonic pulses partially penetrate first surface 52 and then travel inside maxilla 50 eventually reaching second transducer 108. Second transducer 108 receives ultrasonic pulses which propagated through maxilla 50, converts them into analog electrical pulses and sends the electrical pulses to ADC 110 via pulser\receiver 104. The ADC samples the electrical pulses which represent the received pulses and sends the samples to computer 112. The computer records, as a first set of results, the samples which represent the emitted pulses and the samples which represent the received pulses along with the initial locations of the transducers and the initial travel distance TD:

The user scans maxilla 50 according to a desired scanning pattern, for example, by moving first transducer 106 along first surface 52 whilst also moving second transducer 108 along second surface 52' in parallel to the first transducer. As mentioned hereinabove, apparatus 100 can be equipped with automatic scanning means which perform this action instead of the user, either mechanically or electronically. During the scanning process, ADC 110 samples the ultrasonic pulses emitted and received at each new location of the transducers, and computer 112 records sets of samples, along with their corresponding transducer locations and travel distance TD. The computer calculates, for each new location of the transducers, a ratio R between ultrasonic attenuation and travel distance.

According to the teachings of the present invention, ratio R will remain approximately the same as long as penetrating ultrasonic pulses do not encounter an internal structure which causes higher or lower attenuation than its proximate surroundings within the hard tissue, on their travel path from first transducer 106 to second transducer 108. However, if penetrating ultrasonic pulses encounter such an internal structure, then ratio R will necessarily change. FIG. 15 illustrates an example in which ultrasonic pulses traveling inside maxilla 50 encounter signal and\or nasal cavities 60 on their travel path from first transducer 106 to second transducer 108. Since signal and\or nasal cavities 60 are sometimes filled with air, they may cause higher attenuation than cortical 54 and trabecular bone 56. Thus, if ultrasonic pulses traverse cavities 60 vial travel path $TP_1$ and a travel distance $TD_1$, then they will suffer higher attenuation on their way to second transducer 108 than similar pulses traveling an equivalent travel distance $TD_1$ via cortical and trabecular bone only. Alternatively, if the ultrasonic pulses bypass cavities 60 via travel path $TP_2$, they will still suffer higher attenuation because their travel distance will be longer thin $TD_1$. In both scenarios, computer 112 will detect the internal structure (cavities 60), based on the change in ratio R. When computer 112 detects such a change in ratio R, it will notify the user (e.g. by issuing an indication on display 114) that an internal structure lies on the path between first transducer 106 and second transducer 108.

It is yet another particular feature of apparatus 100 that it can measure the depth of an internal structure within hard tissue, such as the depth of the signal and\or nasal cavities in a maxilla, based on changes in ratio R. According to this method, the transducers scan the maxilla as explained heretofore. As soon as computer 112 detects a characteristic change in ratio R, it means that the penetrating ultrasonic pulses have first met cavities 60 on their path from first transducer 106 to second transducer 108. Since the computer receives from location monitoring device 116 the location of the transducers at any given moment, the computer can therefore calculate vertical depth $L_y$ of cavities 60 as the vertical distance from alveolar ridge 64 of maxilla 50 to the location of the transducers which first introduced a characteristic change in ratio R. The measured depth will then be displayed on display 114.

It is still another particular feature of apparatus 100 that it can combine some or all of the above methods to produce an integrated internal image of hard tissue. For example, computer 112 in apparatus 100 can produce and display on display 114 a sectional image of mandible 30 based on such parameters as vertical depth $L_y$, horizontal depth $L_y$, vertical diameter $D_y$ and horizontal diameter $D_x$ of mandibular canal 38 (all obtained using the teachings of the present invention), combined with such additional parameters as vertical width $S_y$ and horizontal width $S_x$ of mandible 30 (obtained using conventional measuring means). Subsequently, computer 112 can further integrate several such sectional images of mandible 30 to create and display a three-dimensional internal image of the mandible.

Referring now to FIG. 11, an alternative embodiment of the present invention, designated 200, will be described. Apparatus 200 is an apparatus for non-invasive ultrasonic imaging of hard tissue. Apparatus 200 is partially similar to apparatus 100, and therefore common elements will be hereunder denoted with the same reference numerals. Apparatus 200 comprises a controller 102 coupled to a pulser\receiver 104 and to a location monitoring device 116. Pulser\receiver 104 is coupled to a transducer 120 capable of emitting and receiving ultrasound, and to an analog-to-digital converter (ADC) 110. ADC 110 is coupled to a computer 112, which is coupled to a display device 114. Location monitoring device 116 is coupled to transducer 120 and to computer 112.

Figure 12:
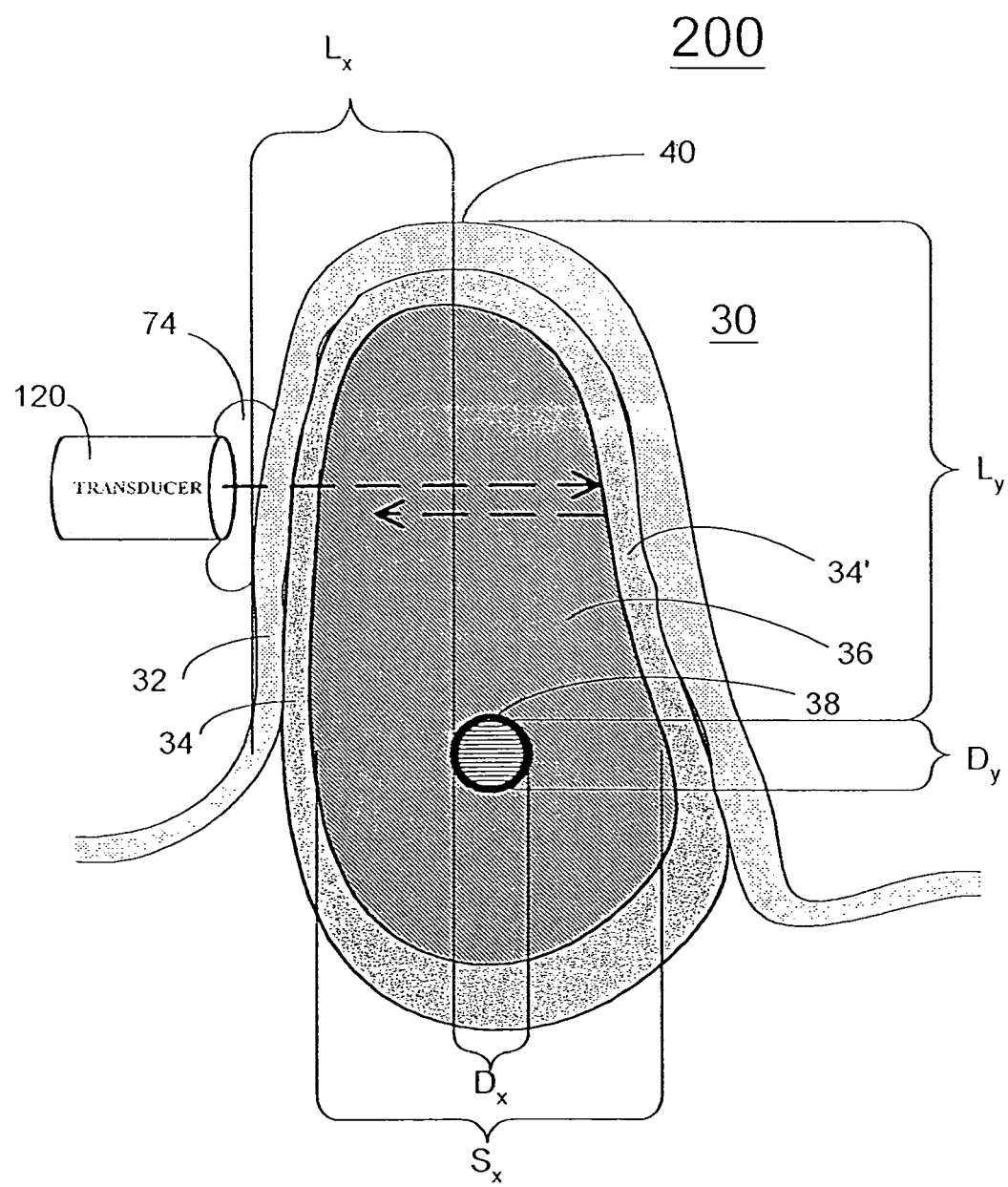
FIG. 12 illustrates the preferred method of operation of the alternative embodiment apparatus of the present invention.

Referring now to FIG. 12 the method of operation of apparatus 200 will be described. Apparatus 200 operates according to a pulse-echo method, as opposed to apparatus 100 which is based on a through-transmission method. A user couples transducer 120 to an initial location on a surface of an organ being examined, for example, on first surface 32 of mandible 30. In FIG. 12, first surface 32 is, for example, a toothless buccal gum surface. As explained hereinabove in reference to transducers 106 and 108 of apparatus 100, the same procedure can be performed on other suitable surfaces inside or outside the mouth cavity. In order to improve penetration of ultrasound signals into the jaw, the user applies coupling material 74 between transducer 120 and surface 32.

When transducer 120 is properly coupled, the user starts the operation of apparatus 200 using controller 102. The controller commands location monitoring device 116 to determine the initial location of transducer 120. Device 116 determines the initial location using a conventional measuring method and sends the result to computer 112. The controller further commands pulser\receiver 104 to generate electrical pulses and to send them to transducer 120. Transducer 120 converts the electrical pulses to ultrasonic pulses and emits them toward first surface 32. The emitted ultrasonic pulses partially penetrate first surface 32 via coupling material 74. Some of the penetrating ultrasonic pulses then travel inside mandible 30 through cortical bone layer 34 and trabecular bone 36. Most of the penetrating pulses travel inside mandible 30 in an approximately straight trajectory (depicted in the drawings as a broken-line arrow). The penetrating ultrasonic pulses are then partially reflected back toward transducer 120 from the opposite cortical bone layer 34'. In some cases, the penetrating pulses may also travel through mandibular canal 38 on their way to opposite surface 34' and after being reflected back toward transducer 120. Transducer 120 receives ultrasonic echoes reflected from within mandible 30, converts them into analog electrical pulses and sends the electrical pulses to ADC 110 via pulser\receiver 104. The ADC samples the electrical pulses which represent the received ultrasonic echo pulses and sends these samples to computer 112. The computer records, as a first set of results, the samples which represent the received pulses along with the initial location of the transducer.

Figure 13A:
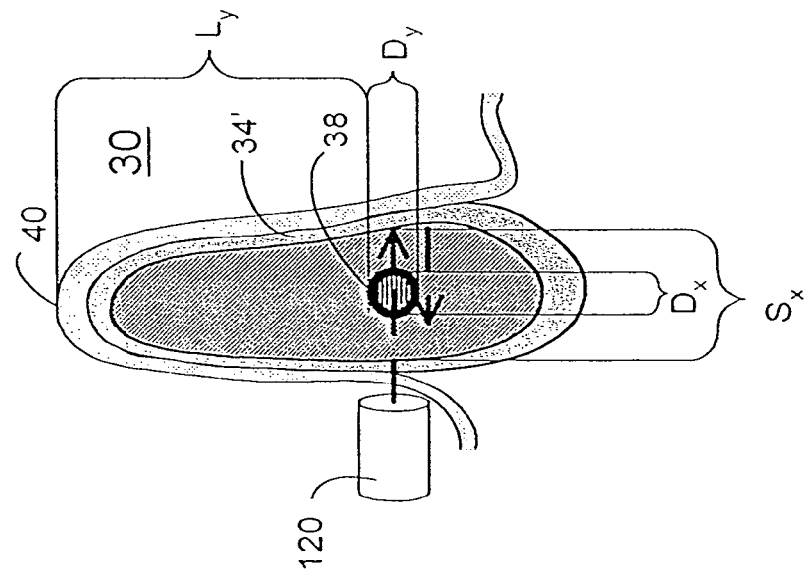
FIGS. 13a-13c illustrate an example of a vertical scanning movement.
Figure 13B:
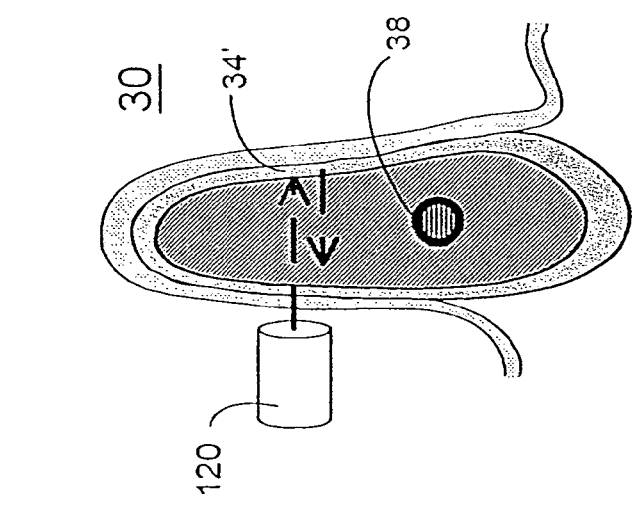
Figure 13C:
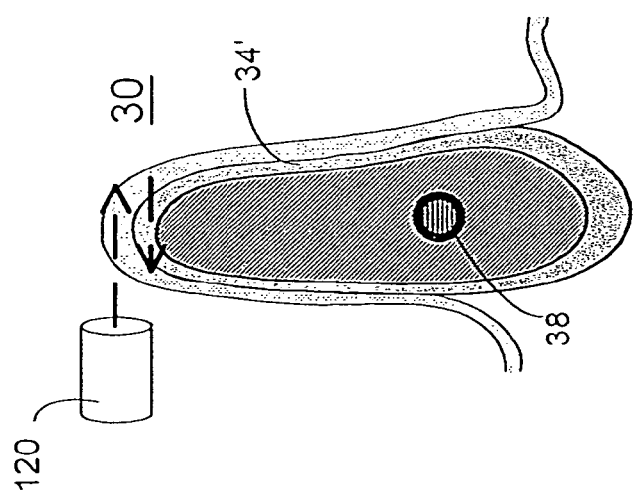
Figure 14A:
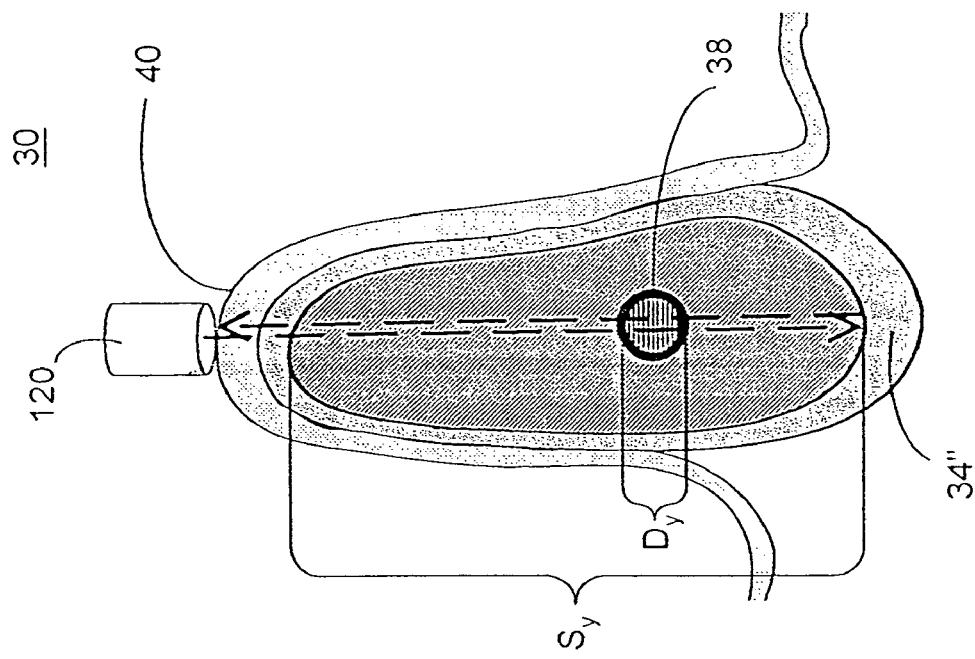
FIGS. 14a-14b illustrate an example of a horizontal scanning movement.
Figure 14B:
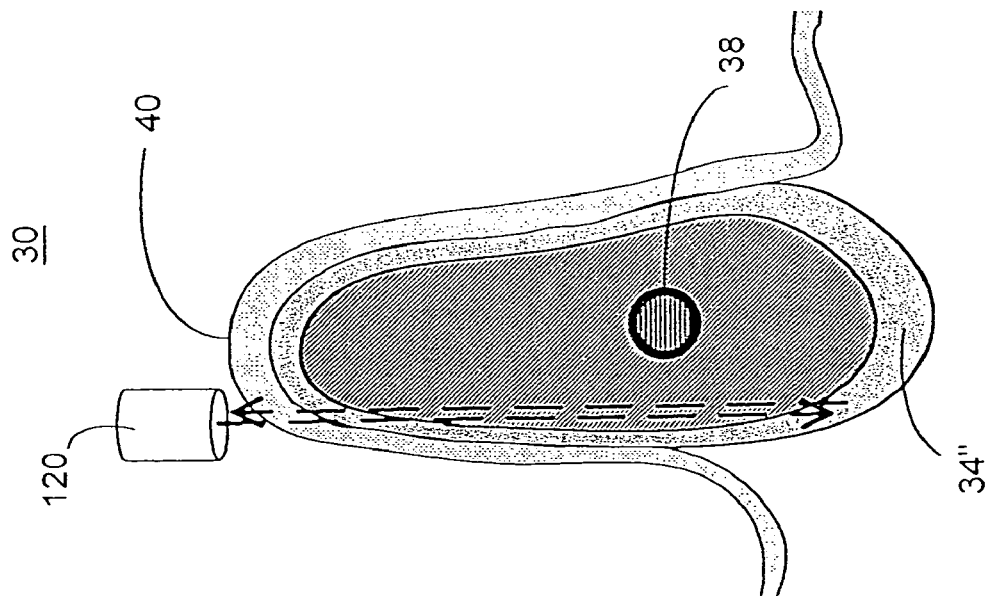

The user scans mandible 30, for example, by moving transducer 120 vertically and\or horizontally along the surface of mandible 30. FIGS. 13a-13c illustrate an example of a vertical scanning movement. FIG. 13a shows the initial location of transducer 120 which is relatively far from mandibular canal 38. FIG. 13b shows the location of the transducer after having been moved approximately halfway closer to mandibular canal 38. FIG. 13c shows the location of the transducer after having been moved further down, so that mandibular canal 38 lies on the ultrasonic travel path (depicted as a broken-line arrow) extending straightforward from the transducer. FIGS. 14a-14b illustrate an example of a horizontal scanning movement of transducer 120 along alveolar ridge 40. FIG. 14a shows the initial location of transducer 120. The transducer is initially placed so that the travel path (depicted as a broken-line arrow) of ultrasonic pulses and echoes does not pass through mandibular canal 38. FIG. 14b shows the transducer after having been moved toward the middle of the jaw, so that mandibular canal 38 lies on the ultrasonic travel path extending straightforward from the transducer.

Alternatively, the user may scan mandible 30 by moving the transducer in a sweeping motion, or by any other desired scanning pattern. Apparatus 200 can further be equipped with automatic mechanical scanning means, for example, a slidable mount to which transducer 120 is attached and which is programmed to execute a desired scanning pattern. Alternatively, apparatus 200 can be equipped with electronic scanning means, for example, an array of transducers instead of single transducer 120.

During the scanning process, ADC 110 samples the ultrasonic pulses received at each new location of the transducers, and computer 112 keeps recording sets of samples along with the corresponding location of the transducer. Computer 112 is programmed to determine certain physical characteristics of the hard tissue being examined, based on an analysis of the recorded sets. As mentioned hereinabove in reference to apparatus 100, the present invention teaches that when, during the scanning process, mandibular canal 38 is situated on the path extending straightforward from transducer 120, consequently computer 112 will detect a local change (increase or decrease) in amplitude of the penetrating pulses.

Hence, it is a particular feature of apparatus 200 that it detects and locates an internal structure within hard tissue (e.g. the mandibular canal in a mandible), by detecting a local change in the amplitude of ultrasonic echo pulses. When computer 112 detects such a local change in the amplitudes it will notify the user (e.g. by issuing an indication on display 114) that the internal structure lies on the path extending straightforward from transducer 120.

It is another particular feature of apparatus 200 that it can measure the depth of an internal structure within hard tissue, for example, the depth of the mandibular canal in a mandible, based on amplitude measurements. Transducer 120 scans mandible 30 according to the method described above.

As soon as computer 112 first detects a characteristic change in the amplitude of received ultrasonic echo pulses, it means that the pulses have first met mandibular canal 38 on their path from first transducer 120 to the surface of reflection. Since the computer receives from location monitoring device 116 the location of the transducer at any given moment, the computer can therefore calculate the depth of mandibular canal as follows. In case of vertical scanning (FIGS. 13a-13c), vertical depth $L_y$ will be calculated as the vertical distance from alveolar ridge 40 to the location of the transducer which first introduced a characteristic change in amplitude. Similarly, in case of horizontal scanning (FIGS. 14a-14b), horizontal depth $L_x$ will be calculated as the horizontal distance from surface 32 to the location of the first characteristic amplitude change.

It is yet another particular feature of apparatus 200 that it can measure the diameter of an internal structure of interest within hard tissue, for example, the diameter of mandibular canal 38 within mandible 30, based on amplitude measurements. Transducer 120 scans mandible 30 according to the method described hereinabove. When measuring horizontal diameter $D_x$ horizontal scanning (FIG. 14) will be performed, and when measuring vertical diameter $D_x$ vertical scanning (FIG. 13) will be performed. As soon as computer 112 first detects a characteristic change in the amplitude of received ultrasonic echo pulses, it means that the pulses have first met mandibular canal 38 on their path from transducer 120 to the surface of reflection. Subsequently, when amplitude returns to its level prior to the characteristic change, it means that the ultrasonic pulses no longer pass through mandibular canal 38. Computer 112 then calculates and displays the diameter of mandibular canal 38 based on the detected borders of the canal and on location information supplied by location monitoring device 116.

It is yet another particular feature of apparatus 200 that it can detect and locate an internal structure within hard tissue, for example mandibular canal 38 within mandible 30, based on spectral function analysis. Transducer 120 scans mandible 30, and ADC 110 sends to computer 112 samples of the received ultrasonic echo pulses, all as explained hereinabove. Computer 112 processes the samples and produces (e.g. using a known FFT algorithm), for each given location of the transducer, a spectral function representing ultrasonic pulses emitted and received at that location. The computer records, for each given location of the transducer, a set containing the spectral function of the received ultrasonic pulses along with the corresponding location of the transducer. Computer 112 can then analyze various characteristics of the spectral functions of the received ultrasonic pulses to determine the location of an internal structure within the hard tissue being examined. As mentioned heretofore in reference to apparatus 100, a frequency shift in the frequency spectrum of the received ultrasonic pulses may indicate the presence of mandibular canal 38 within mandible 30. Hence, when computer 112 detects a characteristic frequency shift in the spectral function of received ultrasonic echo pulses, it will notify the user (e.g. by issuing an indication on display 114) that an internal structure lies on the ultrasonic travel path extending straightforward from transducer 120. After apparatus 200 detects and locates the internal structure of interest, the apparatus may further be used in order to measure the depth of such internal structure using location information supplied by location monitoring device 116, as explained heretofore.

It is yet another particular feature of apparatus 200 that it can detect and locate an internal structure within hard tissue, based on artificially amplified characteristics of the received pulses, such characteristics being indicative of the internal structure. After computer 112 obtains spectral functions of ultrasonic pulses received in various locations along mandible 30 (as explained hereinabove), the computer processes the recorded spectral functions to determine a discrete representative value for each spectral function. As a result, the computer obtains and records a first array of representative values as a function of the locations of the transducer across mandible 30. Following, the computer analyzes the first array, in order to detect a distinct local variability in the representative values. In case such distinct local variability is found, the computer can conclude and notify the user (e.g. on display 114) that the internal structure of interest is situated in the locations corresponding to the locally varying representative values. If no such distinct local variability is detected, the computer will proceed and obtain a second array of representative values, which is based on a different representation criterion than that of the first array. If the first array is, for example, an array of the total sum of amplitudes, then the second array can be, for example, an array of the RMS of amplitudes. The computer analyzes the second array to find a distinct local variability which indicates the presence of the internal structure of interest. If again no such distinct local variability is detected, the computer will perform a predetermined mathematical manipulation on the first and\or second arrays. For example, the computer can divide the first array by the second array to obtain a third, synthetic array of representative values as a function of locations across the mandible. The computer analyzes the third, synthetic array to find a distinct local variability which indicates the presence of the internal structure. The computer may repeat the above procedure a desired number of repetitions.

It is yet another particular feature of apparatus 200 that it enables calculating the diameter of an internal structure within hard tissue, based on analysis of the ratio between the amplitude of received ultrasonic pulses and the attenuation coefficients inside the organ being examined. According to this method, after computer 112 obtains spectral functions of ultrasonic pulses received in various locations along mandible 30 (as explained hereinabove), the computer determines the minimal amplitude $A_3$ of ultrasonic pulses received by transducer 120 during the scanning process, and the maximal amplitude $A_4$ of such pulses. As mentioned hereinabove, the present invention teaches that attenuation in mandibular canal 38 is typically different than in cortical 34 and trabecular bone 36. Where attenuation in the mandibular canal is lower than in cortical and trabecular bone, minimal amplitude $A_3$ will be measured when penetrating ultrasonic pulses do not travel through mandibular canal 38 (FIGS. 13a, 13b or 14a), whereas maximal amplitude $A_4$ will be measured when the pulses travel partly via mandibular canal 38 (FIG. 13c or 14b). The attenuation coefficient inside trabecular bone 36, designated $\gamma_1$, as well as the attenuation coefficient inside mandibular canal 38 (approximately equal to the attenuation coefficient in water) designated $\gamma_2$, are both measured using conventional means and are fed into computer 112.

As mentioned above, it is known in the art that the ratio between the amplitude A of an ultrasonic signal and the distance S traveled by the ultrasonic signal inside a medium with an attenuation coefficient $\gamma$ can be expressed by the following first equation:

$$A \approx e^{-(\gamma \cdot S)}$$

Hence, the ratio between minimal amplitude $A_3$ and trabecular width $S_x$ can be expressed by the sixth equation:

$$A_3 \approx e^{-(\gamma_1 \cdot 2 \cdot S_x)}$$

The ratio between maximal amplitude $A_4$ and diameter $D_x$ of mandibular canal 38 can be expressed by the following seventh equation:

$$A_4 \approx e^{-(\gamma_1 \cdot 2 \cdot (S_x - D_x) + (\gamma_2 \cdot 2 \cdot D_x))}$$

If the seventh equation is divided by the sixth equation, then the following eighth equation is obtained:

$$\frac{A_4}{A_3} = e^{2 \cdot D_x \cdot (\gamma_1 - \gamma_2)}$$

The above eighth equation can be solved for $D_x$ as expressed by the following ninth equation:

$$D_x = \frac{\log \frac{A_4}{A_3}}{2 \cdot (\gamma_1 - \gamma_2)}$$

Thus, having acquired minimal and maximal amplitude measurements $A_3$ and $A_4$, and attenuation coefficients $\gamma_1$ and $\gamma_2$, computer 112 calculates and displays on display 114 horizontal diameter $D_X$ of mandibular canal 38, using the above ninth equation. Vertical diameter $D_x$ can be measured in a similar manner, based on minimal and maximal amplitudes $A_3$ and $A_4$ measured vertically.

It is still another particular feature of apparatus 200 that it can combine some or all of the above methods to produce an integrated internal image of hard tissue. For example, computer 112 in apparatus 200 can produce and display on display 114 a sectional image of mandible 30, based on such parameters as vertical depth $L_y$, horizontal depth $L_x$, vertical diameter $D_y$ and horizontal diameter $D_x$ of mandibular canal 38 (all obtained using the teachings of the present invention), combined with such additional parameters as vertical width $S_y$ and horizontal width $S_x$ of mandible 30 (obtained using conventional measuring means). Subsequently, computer 112 can further integrate several such sectional images of mandible 30 to create and display a three-dimensional internal image of the mandible.

Figure 16:
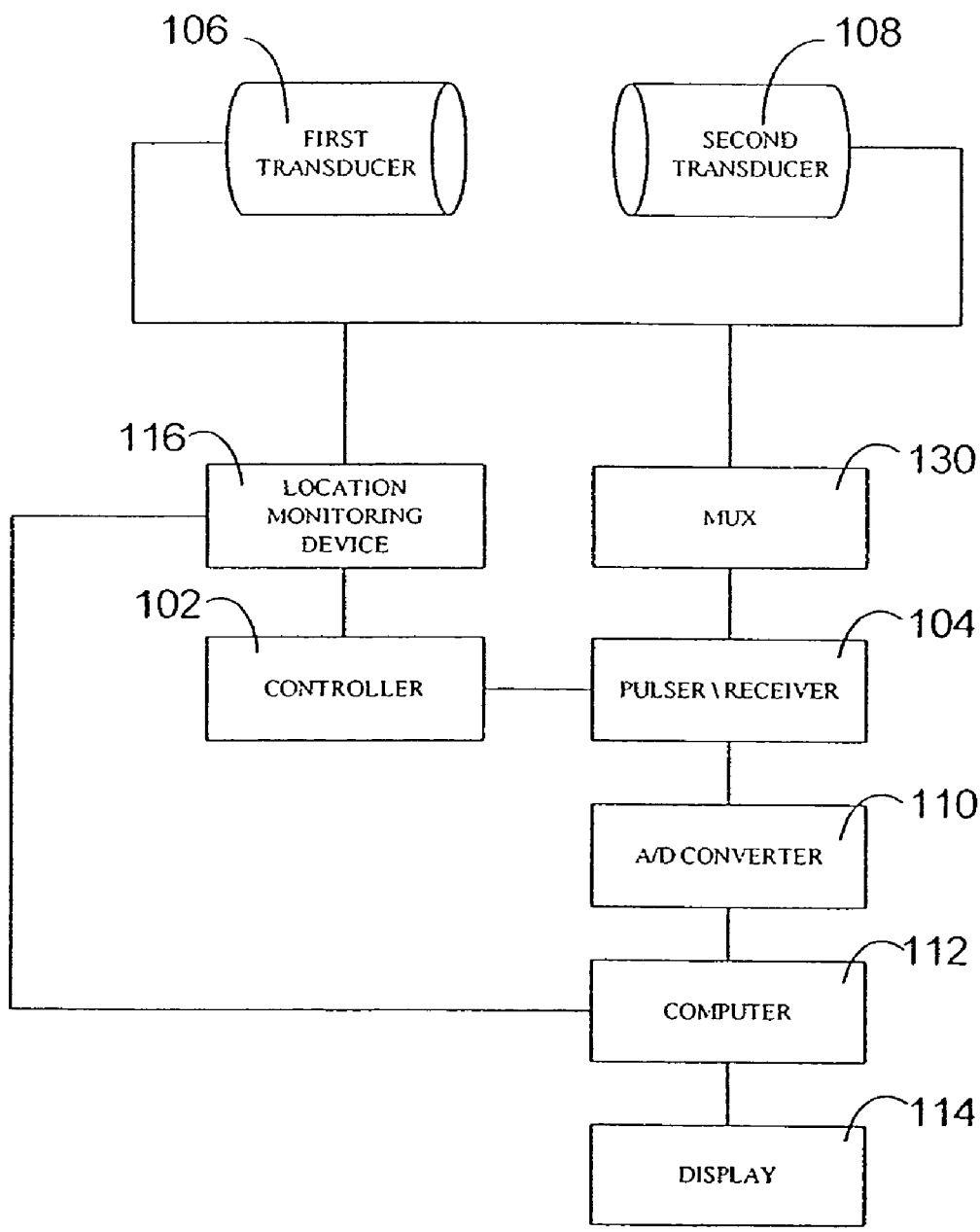
FIG. 16 illustrates yet another alternative embodiment apparatus of the present invention.

Referring now to FIG. 16, yet another alternative embodiment of the present invention, designated 300, will be described. Apparatus 300 is an apparatus for non-invasive ultrasonic imaging of hard tissue. Apparatus 300 is partially similar to apparatuses 100 and 200, and therefore common elements will be hereunder denoted with the same reference numerals. Apparatus 300 comprises a controller 102 coupled to a pulser\receiver 104 and to a location monitoring device 116. Pulse\receiver 104 is coupled to a multiplexer (MUX) 130, which is coupled to a first transducer 106 and to a second transducer 108. Transducers 106 and 108 are capable of emitting and receiving ultrasound. Pulser\receiver 104 is further coupled to an analog-to-digital converter (ADC) 110, coupled to a computer 112, which is coupled to a display device 114. Location monitoring device 116 is coupled to first transducer 106, to second transducer 108, and to computer 112.

Apparatus 300 is capable of operating in several modes of operation. In a first mode of operation, the through-transmission mode, a user sets MUX 130 so that it directs an output electrical signal from pulser\receiver 104 to first transducer 106, and further directs the analog electrical signal which represents the ultrasonic signal received by second transducer 108 back to the pulser\receiver 104. In this mode apparatus 300 actually operates like apparatus 100, as explained hereinabove. In a second mode of operation, the pulse-echo mode, the user sets MUX 130 so that it directs an output electrical signal from pulser\receiver 104 to first transducer 106, and further directs the analog electrical signal which represents the ultrasonic signal received by first transducer 106 back to the pulser\receiver. In this mode apparatus 300 actually operates like apparatus 200, as explained hereinabove. In a third mode of operation, a combined mode, apparatus 300 operates in the first mode to obtain a first set of measurements; and then apparatus 300 operates in the second mode to obtain a second set of measurements; computer 112 records the first and second sets of measurements, and integrates them to produce and display on display 114 an integrated internal image of the hard tissue being examined, for example, a sectional image or a three-dimensional image based on a plurality of sectional images.

Figure 17:
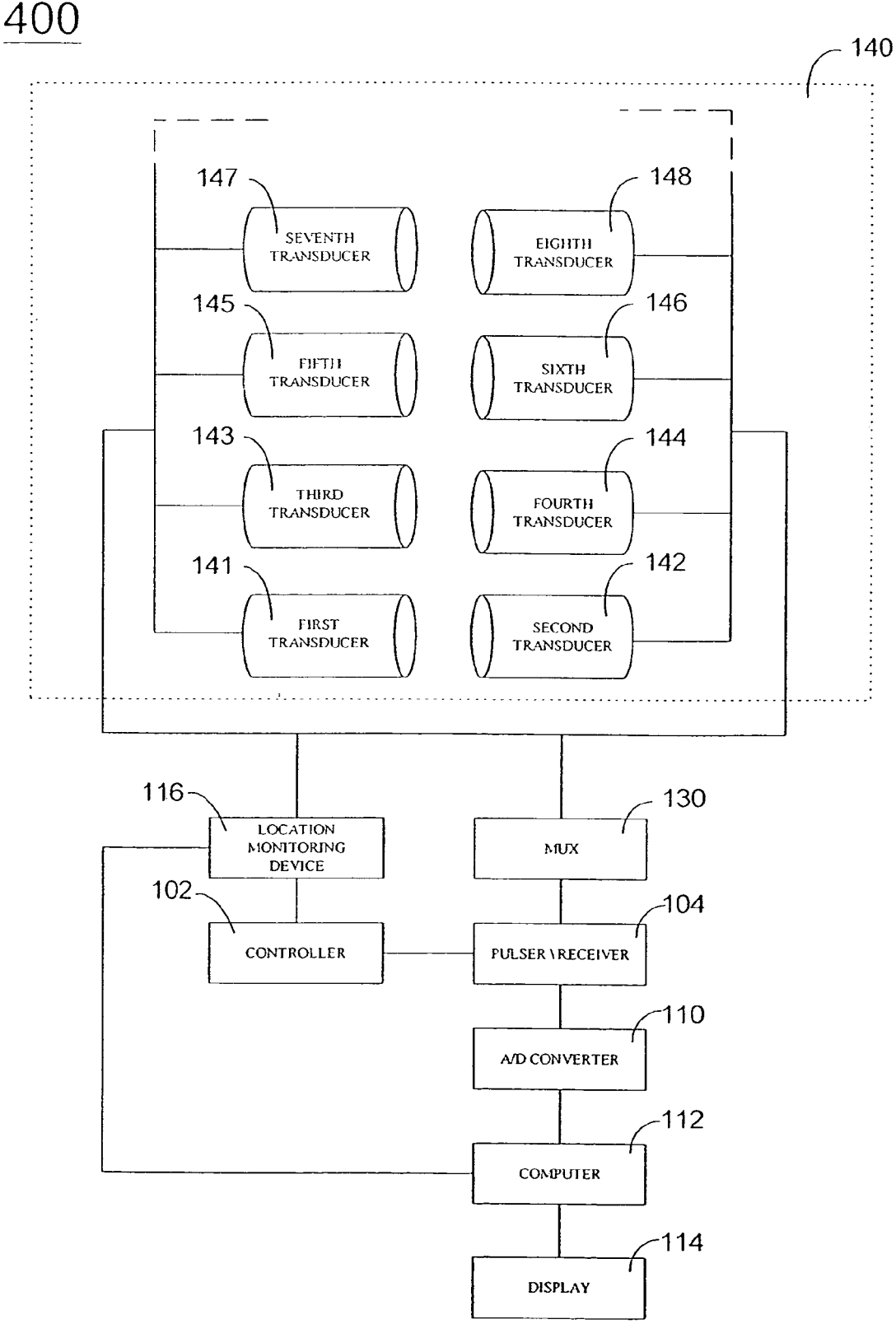
FIG. 17 illustrates still another alternative embodiment apparatus of the present invention.

Referring now to FIG. 17 still another alternative embodiment of the present invention, designated 400, will be described. Apparatus 400 is an apparatus for non-invasive ultrasonic imaging of hard tissue. Apparatus 400 is partially similar to apparatus 300, and therefore common elements will be hereunder denoted with the same reference numerals. Apparatus 400 comprises a controller 102 coupled to a pulser\receiver 104 and to a location monitoring device 116. Pulser\receiver 104 is coupled to a multiplexer (MUX) 130 and also to an analog-to-digital converter (ADC) 110. ADC 110 is coupled to a computer 112 coupled to a display device 114. MUX 130 is further coupled to an array of transducers 140 containing a plurality of transducers, for example, eight transducers 141-148. Each transducer in array 140 is capable of emitting and receiving ultrasound. Apparatus 400 further comprises a location monitoring device 116 coupled to each of the transducers in array 140 and further-coupled to computer 112.

Figure 18:
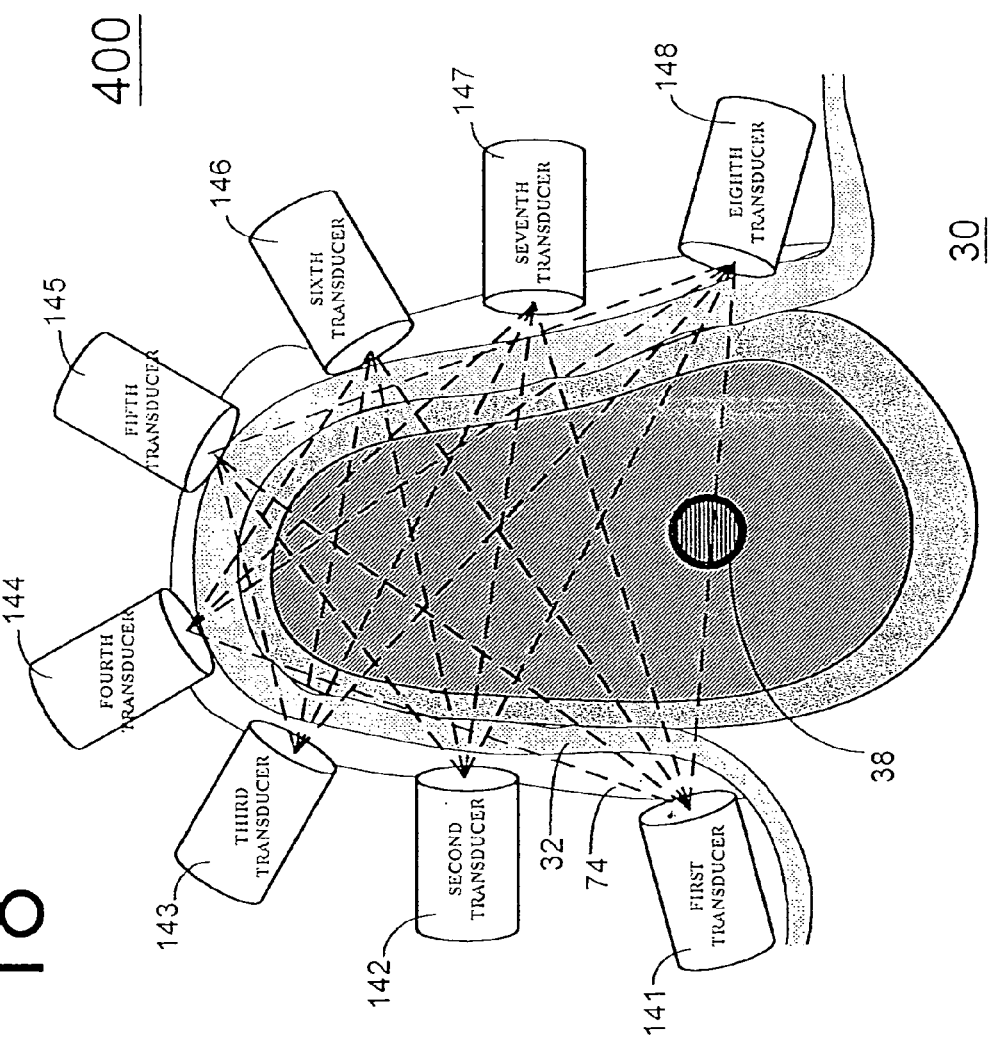
FIG. 18 illustrates the preferred method of operation of another alternative embodiment apparatus of the present invention.

Referring now to FIG. 18, the method of operation of apparatus 400 will be described. A user couples transducers 141-148 to an organ being examined so that at least some of the transducers are facing each other. For example, transducers 141-148 may be placed around a gum surface 32 of a mandible 30 as illustrated in FIG. 18. The user applies a coupling material 74 between each transducer and the surface to which it is coupled, as explained hereinabove in reference to apparatus 100. When the transducers are properly coupled, the user starts the operation of apparatus 400 using controller 102. The controller commands location monitoring device 116 to determine the position of each of the transducers in array 140 with respect to the other transducers therein and with respect to surface 32 to which they are coupled. Device 116 sends the locations to computer 112 which records them.

Next, apparatus 400 electronically scans the organ being examined, as follows. Controller 102 commands pulser\receiver 104 to generate electrical pulses and send them to MUX 130 and to ADC 110. The ADC samples the electrical pulses, and sends to computer 112 the samples which represent the emitted pulses. MUX 130 directs the electrical pulses from pulser\receiver 104 to a first transducer 141. The ultrasonic pulses emitted from first transducer 141 partially penetrate mandible 30 and then travel inside the mandible eventually reaching one or more of the remaining transducers in array 140. The receiving transducers convert the received ultrasonic pulses to analog electrical pulses, and send the latter to MUX 130. The MUX directs analog electrical pulses from the remaining transducers back to ADC 110 via pulser\receiver 104. The ADC samples the electrical pulses and sends the samples, which represent the received ultrasonic pulses, to computer 112. The computer records the digital samples in discrete sets, wherein each set contains samples representing ultrasonic pulses emitted by one certain transducer and received by another certain transducer, along with the locations of these transducers (as determined by device 116). The above procedure is repeated several times, whilst each time a different transducer from array 140 emits ultrasound and the remaining transducers receive ultrasound. FIG. 18 illustrates an example of various possible ultrasonic travel paths (depicted as broken lines) inside mandible 30.

At the end of the scanning process described heretofore, computer 112 will have accumulated a desired number of sets of samples and travel paths. The computer processes the accumulated sets, and converts each set of samples and ultrasonic travel path into a set of a predetermined integral physical quantity and travel path. For example, the computer can calculate, based on samples of the emitted and received ultrasonic pulses in each travel path, the integral attenuation in each travel path. Following, the computer implements a known method, such as a Radon Transform algorithm, in order to deduce from the sets of integral physical quantity and travel path, a physical quantity per each point inside the hard tissue. For example, the computer can use a Radon Transform algorithm for deducing from all the sets of integral attenuation per travel path, the level of attenuation in each discrete point inside the scanned cross-section of the mandible. The computer can then display on display 114 a sectional internal image of mandible 30, based on the deduction algorithm.

It is a particular feature of apparatus 400 that it can detect, locate and measure the size of an internal structure within hard tissue, for example, a mandibular canal 38 in a mandible 30. As mentioned above, the level of ultrasonic attenuation inside mandibular canal 38 is typically different than in cortical 34 and trabecular bone 36. The level of attenuation at each point inside mandible 30 can be determined using apparatus 400 as explained hereinabove. Following, computer 112 of apparatus 400 can detect mandibular canal 38 by finding the locations within mandible 30 that are characterized with an attenuation level other than that of its surroundings. Horizontal depth $L_x$, vertical depth $L_y$, horizontal diameter $D_x$, and vertical diameter $D_y$ (see FIG. 12) of mandibular canal 38, as well as other parameters pertaining to the size and location of the internal structure of interest, can all be calculated based on location information obtained by device 116 and on the Radon Transform internal image of mandible 30.

It is another particular feature of apparatus 400 that it can further integrate several sectional images of the hard tissue being examined, to create and display a three-dimensional internal image of the hard tissue.

Thus, it is evident that the present invention provides a real-time, chair-side, accurate, safe, radiation-free, and economical method and apparatus for non-invasive ultrasonic imaging of hard tissue.

While preferred embodiments of the present invention have been disclosed hereinabove, it is to be understood that these preferred embodiments are given as an example only and are not intended to be limiting. Those skilled in the art may make various modifications and additions to the embodiments used to illustrate the teachings of the present invention and those modifications and additions would remain within the scope of the present invention.

It is emphasized that the present invention is not limited to imaging human jaws. Other uses, including but not limited to imaging other types of human hard tissue, in addition to animal hard tissue, are included in the scope of the present invention.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents, patent applications mentioned in this specification are herein incorporated in their entirety by reference into the specification, to the same extent as if each individual publication, patent, patent application was specifically and individually indicated to be incorporated herein by reference. In addition, citation or identification of any reference in this application shall not be construed as an admission that such reference is available as prior art to the present invention.

What is claimed:

1. An improved ultrasonic imaging system constructed to facilitate imaging of at least a portion of a jaw, the system comprising:
   (a) a probe comprising at least one curved wand whereupon each is mounted a curved array of ultrasonic transducers, wherein at least one said curved wand is designed and constructed to be insertable into a mouth of a patient;
   (b) a position locator module designed and constructed to be capable of defining a location of said probe in six degrees of freedom and transmitting said definition to a central processing unit; and
   (c) said central processing unit capable of;
      (i) receiving from said probe digital data from each of said ultrasonic transducers in each said curved array;
      (ii) further receiving from said position locator a location of said probe; and
      (iii) transforming said digital data into an image of said at least a portion of a jaw.

2. The system of claim 1, wherein said image is a three dimensional image.

3. The system of claim 1, wherein said probe is a mandibular probe designed and constructed to facilitate imaging of at least a portion of a lower jaw and includes:
   (i) a first said curved array of ultrasonic transducers mounted upon a first said curved wand, said first curved array of ultrasonic transducers positionable distal to the lower jaw and outside of said mouth;
   (ii) a second said curved array of ultrasonic transducers, said second curved array of transducers mounted upon a second said curved wand, said second curved array of ultrasonic transducers positionable proximal to the lower jaw and inside of said mouth; and
   (iii) at least one connective member, said connective member designed and constructed to connect said first and second curved wands one to another and to allow relative positioning thereof; wherein said connective member includes an assembly designed and constructed to attach said first and second curved wands and facilitate translational motion of said curved wands with respect to one another.

4. The system of claim 1, wherein said probe is designed and constructed to facilitate imaging of at least a portion of an upper jaw and includes a single curved array of ultrasonic transducers mounted upon a said curve wand, wherein said curved wand is designed and constructed to be insertable into said mouth of said patient.

5. The system of claim 1 wherein said position locator module includes at least one first position sensor located on said probe and at least one second position sensor located on a head of a subject.

6. The system of claim 1 wherein said position locator module includes a first mechanical positioning mechanism designed and constructed to position said probe and a retention means designed and constructed to engage and retain head of said patient in a known position.

7. The system of claim 1, further including an ultrasonic coupling cushion, said cushion comprising an elastic container capable of retaining a coupling medium wherein said elastic container is designed and constructed to be insertable in said mouth of said patient.

8. A method of producing an ultrasonic image of at least a portion of a jaw, the method comprising:
  (a) providing a probe comprising at least one curved wand whereupon each is mounted a curved array of ultrasonic transducers, wherein at least one said curved wand is designed and constructed to be insertable into a mouth of a patient.
  (b) defining a location of said probe in six degrees of freedom by means of a position locator;
  (c) communicating said location to a central processing unit;
  (d) transmitting an ultrasonic signal from at least one of said transducers and receiving at least a portion of said ultrasonic signal at least one of said transducers; and
  (e) employing a central processing unit to;
    (i) receive a set of digital data pertaining to said transmitting and receiving performed by said transducers in each said curved array of said probe;
    (ii) further receive from said position locator a location of said probe; and
    (iii) transform said digital data into an image of said at least a portion of the jaw.

9. The method of claim 8, wherein said image is a three dimensional image.

10. The method of claim 8, wherein providing a probe includes providing a mandibular probe designed and constructed to facilitate imaging of at least a portion of a lower jaw and includes:
  (i) providing a first said curved array of ultrasonic transducers mounted upon a first said curved wand, said first curved array of ultrasonic transducers positionable distal to the lower jaw and outside of said mouth;
  (ii) providing a second said curved array of ultrasonic transducers, said second curved array of transducers mounted upon a second said curved wand, said second curved array of ultrasonic transducers positionable proximal to the lower jaw and inside of said mouth;
  (iii) providing at least one connective member, said connective member designed and constructed to connect said first and second curved arrays one to another and to allow relative positioning thereof; and wherein said connective member includes an assembly designed and constructed to attach said first and second curved wands and facilitate translational motion of said curved wands with respect to one another.

11. The method of claim 8, wherein providing a probe includes providing a maxillary probe designed and constructed to facilitate imaging of at least a portion of an upper jaw and includes a single said curved array of ultrasonic transducers mounted upon a said curved wand, wherein said curved wand is designed and constructed to be insertable into said mouth of said patient.

* * * * *